United States Patent
Shinohata et al.

(10) Patent No.: US 9,950,273 B2
(45) Date of Patent: Apr. 24, 2018

(54) METHOD OF SEPARATION

(75) Inventors: Masaaki Shinohata, Tokyo (JP);
Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 13/821,658

(22) PCT Filed: Mar. 30, 2012

(86) PCT No.: PCT/JP2012/058625
§ 371 (c)(1),
(2), (4) Date: Mar. 8, 2013

(87) PCT Pub. No.: WO2013/111353
PCT Pub. Date: Aug. 1, 2013

(65) Prior Publication Data
US 2014/0332367 A1    Nov. 13, 2014

(30) Foreign Application Priority Data

Jan. 25, 2012    (JP) ............................ P2012-013094
Jan. 25, 2012    (JP) ............................ P2012-013117

(51) Int. Cl.
*B01D 3/00* (2006.01)
*C07C 263/20* (2006.01)
(Continued)

(52) U.S. Cl.
CPC ............ *B01D 3/009* (2013.01); *C07C 263/20* (2013.01); *C07C 269/08* (2013.01);
(Continued)

(58) Field of Classification Search
CPC ...... B01D 3/009; B01D 3/4249; B01J 19/002; B01J 19/0053; B01J 19/30; B01J 19/305;
(Continued)

(56) References Cited

U.S. PATENT DOCUMENTS 3,493,218 A * 2/1970 Castellucci ............ B01D 53/18
                                                                261/95
4,379,736 A    4/1983 Kendall et al.
(Continued)

FOREIGN PATENT DOCUMENTS

CN    1164529 A    11/1997
CN    1660793 A    8/2005
(Continued)

OTHER PUBLICATIONS

Sulzer Chemtech, Structured Packings for Separation and Reactive Distillation, revised 2002/2003, published online Oct. 16, 2004.*
(Continued)

*Primary Examiner* — Prem C Singh
*Assistant Examiner* — Brandi M Doyle
(74) *Attorney, Agent, or Firm* — Morgan, Lewis & Bockius LLP

(57) ABSTRACT

The present invention provides a separation method of separating (A) and (B), comprising: a step of separating at least either an active hydrogen-containing compound (A) or a compound (B) that reversibly reacts with (A) from a mixture containing (A) and (B) by distillation in a multistage distillation column; and a step of supplying the mixture to an inactive region formed within the multistage distillation column.

5 Claims, 14 Drawing Sheets

(51) Int. Cl.
    *C07C 269/08*     (2006.01)
    *C07C 331/30*     (2006.01)

(52) U.S. Cl.
    CPC ........ *C07C 331/30* (2013.01); *C07C 2601/14* (2017.05); *Y02P 20/127* (2015.11)

(58) Field of Classification Search
    CPC .......................... B01J 19/32; B01J 2204/002; B01J 2219/304; B01J 2219/30416; B01J 2219/30425; B01J 2219/30433; C07C 37/74; C07C 41/42; C07C 263/20; C07C 265/14; C07C 269/08; C07C 331/30; C07C 271/12; C07C 271/44; C07C 2101/14; Y02P 20/127
    USPC ...................................... 203/28–38; 202/262
    See application file for complete search history.

(56) References Cited

U.S. PATENT DOCUMENTS

| | | | |
|---|---|---|---|
| 5,348,710 A * | 9/1994 | Johnson ..................... | B01J 8/02 203/DIG. 6 |
| 5,731,453 A | 3/1998 | Nishihira et al. | |
| 2003/0050424 A1 | 3/2003 | Bernard | |
| 2005/0222291 A1 | 10/2005 | Pirkl et al. | |
| 2007/0270604 A1 | 11/2007 | Fukuoka et al. | |
| 2008/0228002 A1 | 9/2008 | Aldrett-Lee et al. | |
| 2008/0237027 A1 * | 10/2008 | Garton et al. ................. | 203/38 |
| 2011/0092731 A1 | 4/2011 | Shinohata et al. | |

FOREIGN PATENT DOCUMENTS

| | | |
|---|---|---|
| CN | 102026965 A | 4/2011 |
| CN | 102105439 | 6/2011 |
| EA | 010425 B1 | 8/2008 |
| EP | 0692469 A1 | 1/1996 |
| EP | 0975404 B1 | 8/2004 |
| EP | 2380659 A1 | 10/2011 |
| GB | 1362708 | 8/1974 |
| JP | S58-110526 A | 7/1983 |
| JP | H05-194352 A | 8/1993 |
| JP | H09-249633 A | 9/1997 |
| JP | H09-301920 A | 11/1997 |
| JP | 2003-147042 A | 5/2003 |
| JP | 2003-284942 A | 10/2003 |
| JP | 2005-225879 A | 8/2005 |
| JP | 2007-521242 A | 8/2007 |
| JP | 2001-323042 A | 11/2011 |
| TW | 200846389 A | 12/2008 |
| WO | 87/05600 A1 | 9/1987 |
| WO | 1999/038859 A1 | 8/1999 |
| WO | 2005/040084 A1 | 5/2005 |
| WO | 2008/128004 A1 | 10/2008 |
| WO | 2009/071533 A1 | 6/2009 |

OTHER PUBLICATIONS

International Preliminary Report on Patentability issued in counterpart PCT/JP2012/058625 dated Aug. 7, 2014.

International Search Report issued in corresponding International Application No. PCT/JP2012/058625 dated Jun. 19, 2012.

Salehi et al., "Statistical analysis of compressive strength data of ceramic Raschig rings fabricated by an extrusion process using a Weibull distribution," Journal of Ceramic Processing Research, 9: 167-171 (2008).

* cited by examiner

METHOD OF SEPARATION

TECHNICAL FIELD

The present invention relates to a separation method. More particularly, the present invention relates to a method of separating a mixture containing a plurality of compounds that reversibly react with each other.

BACKGROUND ART

Distillation is generally used for separating a gas composition composed of a plurality of components. Distillation is an operation of condensing a specific component of a mixture utilizing the difference in vapor pressure between the component substances. By heating a mixture to be distilled, each component is gradually evaporated from the surface, and boiling starts when the sum of vapor pressures of the components is consistent with the pressure of the system. The composition of the generated vapor is then almost determined from both the component composition of the surface and the vapor pressures (partial pressures) of the components at that temperature according to the Raoult's law. Batch distillation and continuous distillation are known as industrial distillation methods.

The evaporation behavior does not involve reaction between the components to be separated. On the other hand, an evaporation behavior involving reaction between gas components, between liquid layer components or between gas-liquid layer components is a complex evaporation behavior.

For example, conventionally, when the equilibrium of an equilibrium reaction is not biased toward the system of formation, the reaction efficiency (equilibrium conversion rate) is generally increased by separating at least one of the products from the reaction system and biasing the equilibrium toward the system of formation. Various methods are known as methods for separating a product from the reaction system. Among these, distillation separation is one of the methods most commonly performed. A method of allowing the reaction to proceed by shifting the equilibrium reaction toward the system of formation while removing a product from the reaction system by distillation is called reactive distillation. For example, Non Patent Literature 1 describes the explanation of reactive distillation by presenting specific examples.

Reactive distillation is generally implemented using a distillation column such as a continuous multistage distillation column. When reactive distillation is performed in a distillation column, a higher-boiling component contained in the reaction liquid is distributed more in a lower stage of the distillation column and a lower-boiling component is distributed more in an upper stage of the distillation column in accordance with the progress of the reaction. Accordingly, in a distillation column, the temperature in the column (liquid temperature) decreases from the bottom to the top of the column. The reaction rate of an equilibrium reaction decreases as the temperature decreases. For this reason, when reactive distillation is performed in the distillation column, the reaction rate decreases from the bottom to the top of the column. Specifically, the reaction efficiency of the equilibrium reaction decreases from the bottom to the top of the column.

In this context, further raising the temperature in the column has been studied to improve the reaction efficiency (i.e., to increase the reaction rate). Patent Literature 1 discloses a method of allowing the reaction to advantageously proceed by supplying a solvent to a reactive distillation column to raise the temperature in the reactive distillation column as a method of efficiently performing an equilibrium reaction represented by Raw material (P)+Raw material (Q)<=>Product (R)+Product (S) (e.g., ester exchange reaction).

However, it is difficult to separate a raw material or a product by distillation while suppressing an undesired reversible reaction as much as possible in a system involving the above-described equilibrium reaction represented by Raw material (P)+Raw material (Q)<=>Product (R)+Product (S), or in a system involving an equilibrium reaction represented by Raw material (P)<=>Product (R)+Product (S). In general, distillation separation is often performed in a high temperature condition even under reduced pressure, and it is difficult to suppress an undesired reversible reaction. For example, it is often undesirable to apply the above-described method to separation by distillation of a mixture containing an active hydrogen-containing compound and a compound that reversibly reacts with the active hydrogen-containing compound, for example.

Examples involving such an undesired reversible reaction include separation of an unreacted monomer by distillation in a method of producing a trifunctional or higher functional polyisocyanate by polymerizing a difunctional isocyanate monomer. In contrast, for example, Patent Literature 1 describes the fact that an allophanated isocyanate was obtained by a method of reacting isophorone diisocyanate with a partially propoxylated glycerol and then removing the unreacted monomer using a thin film evaporator. Patent Literature 2 also describes the fact that an allophanated isocyanate was obtained by a method of reacting hexamethylene diisocyanate with 1-butanol and then removing the excess monomer by continuous distillation.

CITATION LIST

Patent Literature

Patent Literature 1: WO 2009/071533
Patent Literature 2: U.S. Patent Application Publication No. 2003/0050424

Non Patent Literature

Non Patent Literature 1: "Kagaku Kogaku" [Chemical Engineering], Vol. 57, No. 1, pp. 77-79 (1993)

SUMMARY OF INVENTION

Technical Problem

In the methods described in Patent Literatures 1 and 2, the system is set at a temperature as low as possible under reduced pressure when the unreacted monomer is removed after allophanation reaction. However, in distillation separation, the system must be set at a temperature equal to or higher than that of allophanation reaction, because an isocyanate used for allophanation reaction or the like generally has a high boiling point. Therefore, allophanation reaction proceeds even during distillation separation, so that a compound may be prepared whose viscosity is higher than the viscosity initially intended, or a gel may be generated.

In this manner, it is often still difficult to perform distillation separation while suppressing an undesired reversible reaction as much as possible in a system involving the above-described equilibrium reaction, and there is a need for a solution to this problem.

An object of the present invention is to provide a separation method that enables at least one compound to be efficiently separated by distillation from a mixture containing a plurality of compounds that reversibly react with each other.

Solution to Problem

As a result of extensive studies to achieve the above object, the present inventors have found that the above object can be achieved by a method of separating a mixture containing an active hydrogen-containing compound (A) and a compound (B) that reversibly reacts with (A) using a multistage distillation column by supplying the mixture to a specific region formed within the multistage distillation column and distilling (A) and (B) in the multistage distillation column, and this finding has led to the completion of the present invention.

Specifically, the present invention is as follows:

[1] A separation method of separating (A) and (B), comprising:

a step of separating at least either an active hydrogen-containing compound (A) or a compound (B) that reversibly reacts with (A) from a mixture containing (A) and (B) by distillation in a multistage distillation column; and a step of supplying the mixture to an inactive region formed within the multistage distillation column.

[2] The separation method according to [1], wherein (A) is a compound having a hydrogen atom bonded to a heteroatom or a halogen atom.

[3] The separation method according to [1] or [2], wherein (A) is a compound having at least one group selected from the group consisting of a group represented by the following formula (1), a group represented by the following formula (2), a group represented by the following formula (3) and a group represented by the following formula (4):

[Chemical Formula 1]

—NH$_2$      (1)

[Chemical Formula 2]

—X$^1$H      (2)

[Chemical Formula 3]

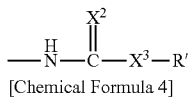      (3)

[Chemical Formula 4]

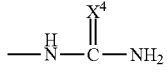      (4)

[wherein X$^1$, X$^2$, X$^3$ and X$^4$ each independently represent an oxygen atom or a sulfur atom, and R' represents an organic group].

[4] The separation method according to any one of [1] to [3], wherein (B) is a compound having a carbonyl group.

[5] The separation method according to any one of [1] to [4], wherein (B) is a compound having at least one group selected from the group consisting of a group represented by the following formula (5), a group represented by the following formula (6), a group represented by the following formula (7) and a group represented by the following formula (8):

[Chemical Formula 5]

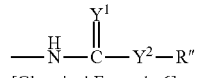      (5)

[Chemical Formula 6]

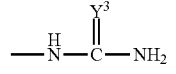      (6)

[Chemical Formula 7]

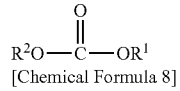      (7)

[Chemical Formula 8]

      (8)

[wherein Y$^1$, Y$^2$, Y$^3$ and Y$^4$ each independently represent an oxygen atom or a sulfur atom, R$^1$ and R$^2$ each independently represent an organic group having 1 to 30 carbon atoms, and R" represents an organic group].

[6] The separation method according to any one of [1] to [5], wherein the multistage distillation column is a plate column, and the inactive region is a region in which the surface contacting with the mixture is formed of a material inactive to the reaction between (A) and (B).

[7] The separation method according to any one of [1] to [5], wherein the multistage distillation column is a packed column, and the inactive region is a region in which the surface contacting with the mixture is packed with a packing material formed by a material inactive to the reaction between (A) and (B).

[8] The separation method according to [6] or [7], wherein the inactive material is a material in which the Fe atom content, the Ni atom content and the Ti atom content are each 10 mass % or less.

[9] The separation method according to any one of [1] to [8], wherein (X) the area of the inner surface of the multistage distillation column contacting with the mixture (unit: m$^2$) and (Y) the volume of the mixture (unit: m$^3$)

satisfy (X)/(Y)≤100.

[10] The separation method according to any one of [1] to [9], wherein the step of distillation separation is performed in the presence of a compound (C) that has a normal boiling point between the normal boiling point of (A) and the normal boiling point of (B) and is chemically inactive to (A) and (B).

[11] The separation method according to any one of [1] to [10], wherein (A) is a compound represented by the following formula (9):

[Chemical Formula 9]

$$R^3\text{−}(X^5\text{−}H)_a \qquad (9)$$

[wherein $R^3$ represents an organic group having 1 to 44 carbon atoms, $X^5$ represents an oxygen atom or a sulfur atom, and a represents an integer of 1 to 6].

[12] The separation method according to any one of [1] to [11], wherein (B) is a compound represented by the following formula (10):

[Chemical Formula 10]

$$R^4\text{−}(N\!=\!C\!=\!Y^5)_b \qquad (10)$$

[wherein $R^4$ represents an organic group having 1 to 80 carbon atoms, $Y^5$ represents an oxygen atom or a sulfur atom, and b represents an integer of 1 to 10].

Advantageous Effects of Invention

According to the present invention, an active hydrogen-containing compound or a compound that reversibly reacts with the active hydrogen-containing compound can be efficiently separated and recovered from a mixture containing the active hydrogen-containing compound and the compound that reversibly reacts with the active hydrogen-containing compound.

DESCRIPTION OF EMBODIMENTS

Figure 1:
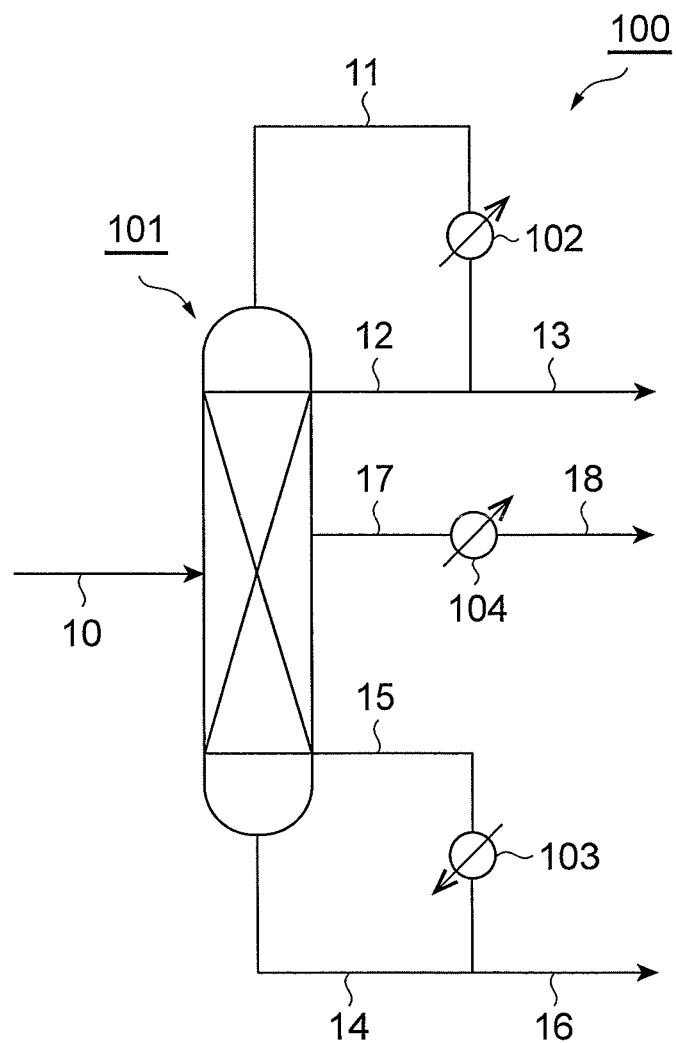
FIG. 1 is an illustration showing a distillation separation unit according to an embodiment.

Embodiments for implementing the present invention will be described in detail below. The present invention is not limited to the following embodiments, and various modifications can be implemented within the spirit of the present invention.

The separation method of the present embodiment is a separation method of separating (A) and (B), comprising: a step of separating at least either an active hydrogen-containing compound (A) (herein also simply called "compound (A)" or "(A)") or a compound (B) that reversibly reacts with (A) from a mixture containing (A) and (B) by distillation in a multistage distillation column; and a step of supplying the mixture to an inactive region formed within the multistage distillation column.

In general, the reversible reaction is a reaction where reaction from the original system (raw material) to the system of formation (product) (forward reaction) occurs together with reaction from the system of formation back to the original system (reverse reaction). In the present embodiment, the "compound (B) that reversibly reacts with the active hydrogen-containing compound (A)" (herein also simply called "compound (B)" or "(B)") is a compound that can form a coupled product of (A) and (B) by reacting with the active hydrogen-containing compound (A). For example, it is a compound that establishes a reaction system represented by the following formula (11).

[Chemical Formula 11]

Active hydrogen-containing compound (A)+Compound (B) that reversibly reacts with the active hydrogen-containing compound→Coupled product of (A) and (B)  (11)

In general, if only forward reaction and reverse reaction of those compounds occur in a reaction system, the reaction system is eventually brought into an equilibrium state containing certain amounts of the substrates and the product. Such a reaction system that can form an equilibrium state is called equilibrium reaction. Specifically, the "compound (B) that reversibly reacts with the active hydrogen-containing compound (A)" may also be called "compound (B) that can form equilibrium reaction with the active hydrogen-containing compound (A)". In the present embodiment, the mixture containing (A) and (B) is preferably such a mixture in which (A), (B), and a coupled product of (A) and (B) are in an equilibrium state represented by the following formula (12).

[Chemical Formula 12]

(A)+(B)⇌Coupled product of (A) and (B)  (12)

More preferably, (B) is a compound that can form thermal dissociation equilibrium with (A), and still more preferably, (A), (B), and a coupled product of (A) and (B) are in a thermal dissociation equilibrium state in the mixture. Thermal dissociation is a reaction in which a molecule or the like is decomposed by a rise in temperature and brought back to the original molecule by reverse reaction upon temperature decrease. In the formula (12), for example, it is a reaction in which a coupled product of (A) and (B) is decomposed by a rise in temperature to form (A) and (B), and (A) reacts with (B) upon temperature decrease to form a coupled product of (A) and (B). Although a catalyst may or may not exist in the reaction system, a reaction system in which a catalyst does not exist is preferred.

In the present embodiment, (B) may be a compound that can react with (A) to form a coupled product of (A) and (B) and that establishes a reaction system represented by the following formula (13).

[Chemical Formula 13]

Active hydrogen-containing compound (A)+Compound (B) that reversibly reacts with the active hydrogen-containing compound→Reaction product (1) of (A) and (B)+Reaction product (2) of (A) and (B)+     (13)

Examples of (A) that can form a reaction system represented by the formula (13) include compounds having a hydrogen atom bonded to a heteroatom or a halogen atom. The "heteroatom" herein refers to an atom other than a carbon atom which can form a heterocyclic compound, for example, an oxygen atom, a sulfur atom and a nitrogen atom.

Examples of the compounds having a hydrogen atom bonded to a heteroatom include compounds having at least one group selected from the group consisting of groups represented by the following formulas (1) to (4):

[Chemical Formula 14]

    (1)

[Chemical Formula 15]

    (2)

[Chemical Formula 16]

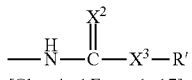    (3)

[Chemical Formula 17]

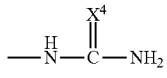    (4)

wherein $X^1$, $X^2$, $X^3$ and $X^4$ ($X^1$ to $X^4$) each independently represent an oxygen atom or a sulfur atom, and R' represents an organic group.

Examples of such compounds include compounds represented by the following formula (14):

[Chemical Formula 18]

    (14)

wherein $R^3$ represents an organic group having 1 to 85 carbon atoms, $X^6$ represents at least one group selected from the group consisting of groups represented by the formulas (1) to (4), and a represents an integer of 1 to 6.

Examples of $R^3$ in the formula (14) include an aliphatic group, an aromatic group, or a group prepared by bonding an aliphatic group and an aromatic group to each other. More specific examples include an acyclic hydrocarbon group, a cyclic hydrocarbon group (e.g., a monocyclic hydrocarbon group, a fused polycyclic hydrocarbon group, a crosslinked cyclic hydrocarbon group, a spiro hydrocarbon group, a ring assembly hydrocarbon group, a cyclic hydrocarbon group with a side chain, a heterocyclic group, a heterocyclic spiro group, a hetero crosslinked ring group or a heterocyclic group), a group in which one or more groups selected from the group consisting of the acyclic hydrocarbon groups and the cyclic hydrocarbon groups are bonded to each other, or a group in which one or more groups selected from the above-described group are bonded to each other via a covalent bond with a specific non-metal atom (carbon, oxygen, nitrogen, sulfur or silicon).

$R^3$ is particularly preferably a group selected from an aliphatic group, an aromatic group, and a group prepared by bonding an aliphatic group and an aromatic group to each other and having 1 to 44 carbon atoms, because a side reaction is less likely to occur. It is preferably a group having 1 to 30 carbon atoms, and more preferably a group having 1 to 13 carbon atoms, taking fluidity and the like into consideration.

When $X^6$ is a group represented by the formula (1), the compound represented by the formula (14) is an organic primary amine. When $X^6$ is a group represented by the formula (2), the compound represented by the formula (14) is a hydroxy compound (if $X^1$ is an oxygen atom) or a thiol (if $X^1$ is a sulfur atom). When $X^6$ is a group represented by the formula (3), the compound represented by the formula (14) is an N-substituted carbamic acid ester (if $X^2$ and $X^3$ are oxygen atoms), an N-substituted O-substituted thiocarbamic acid ester (if $X^2$ is a sulfur atom and $X^3$ is an oxygen atom), an N-substituted S-substituted thiocarbamic acid ester (if $X^2$ is an oxygen atom and $X^3$ is a sulfur atom) or an N-substituted dithiocarbamic acid ester (if $X^2$ and $X^3$ are sulfur atoms). When $X^6$ is a group represented by the formula (4), the compound represented by the formula (14) is an N-substituted ureido (if $X^4$ is an oxygen atom) or an N-substituted thioureido (if $X^4$ is a sulfur atom).

The organic primary amine represented by the formula (14) is 1) an aromatic organic primary monoamine where $R^3$ is a group having 6 to 85 carbon atoms which contains one or more optionally aliphatically and/or aromatically substituted aromatic rings, the aromatic ring in $R^3$ is substituted with an $NH_2$ group, and a is 1, 2) an aromatic organic primary polyamine where $R^3$ is a group having 6 to 44 carbon atoms which contains one or more optionally aliphatically and/or aromatically substituted aromatic rings, the aromatic ring in $R^3$ is substituted with an $NH_2$ group, and a is 2 or more, or 3) an aliphatic organic primary polyamine where $R^3$ is an optionally aromatically substituted aliphatic group having 1 to 44 carbon atoms, and a is 2 or 3.

The organic primary amine where the atom (preferably a carbon atom) with an $NH_2$ group bonded thereto is contained in an aromatic ring is described as an aromatic organic amine, and the organic primary amine where such an atom is bonded to an atom (mainly carbon) not in an aromatic ring is described as an aliphatic organic amine.

Examples of such $R^3$ include linear hydrocarbon groups such as methylene, dimethylene, trimethylene, tetramethylene, pentamethylene, hexamethylene and octamethylene; groups derived from unsubstituted alicyclic hydrocarbons such as cyclopentane, cyclohexane, cycloheptane, cyclooctane and bis(cyclohexyl)alkane; groups derived from alkyl-substituted cyclohexanes such as methylcyclopentane, ethylcyclopentane, methylcyclohexane (each isomer), ethylcyclohexane (each isomer), propylcyclohexane (each isomer), butylcyclohexane (each isomer), pentylcyclohexane (each isomer) and hexylcyclohexane (each isomer); groups derived from dialkyl-substituted cyclohexanes such as dimethylcyclohexane (each isomer), diethylcyclohexane (each isomer) and dibutylcyclohexane (each isomer); groups derived from trialkyl-substituted cyclohexanes such as 1,5, 5-trimethylcyclohexane, 1,5,5-triethylcyclohexane, 1,5,5-tripropylcyclohexane (each isomer) and 1,5,5-tributylcyclohexane (each isomer); groups derived from monoalkyl-substituted benzenes such as toluene, ethylbenzene and propylbenzene; groups derived from dialkyl-substituted benzenes such as xylene, diethylbenzene and dipropylbenzene; and groups derived from aromatic hydrocarbons such as diphenylalkane and benzene. Particular examples include groups derived from hexamethylene, phenylene, diphenylmethane, toluene, cyclohexane, xylenyl, methylcyclohexane, isophorone and dicyclohexylmethane.

The hydroxy compound is an alcohol or an aromatic hydroxy compound, and if the hydroxy compound is an alcohol, it is a compound represented by the following formula (15):

[Chemical Formula 19]

(15)

wherein $R^3$ represents an aliphatic group having 1 to 44 carbon atoms, or a group having 7 to 44 carbon atoms and composed of an aliphatic group with an aromatic group bonded thereto, which is substituted with c hydroxy group(s), and c represents an integer of 1 to 6, provided that $R^3$ is a group having active hydrogen only in the hydroxy group(s), and the —OH group of the alcohol represented by the formula (15) is an —OH group not bonded to the aromatic group.

Preferred examples of $R^3$ in the formula (15) include a methyl group, an ethyl group, a propyl group, a butyl group, a pentyl group, a hexyl group, a heptyl group, an octyl group, a nonyl group, a decyl group, a dodecyl group, an octadecyl group, a cyclopentyl group, a cyclohexyl group, a cycloheptyl group, a cyclooctyl group, a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group and a dibutylcyclohexyl group.

Specific examples of the alcohol having such $R^3$ include methanol, ethanol, propanol, butanol, pentanol, hexanol, heptanol, octanol, nonanol, decanol, dodecanol, octadecanol, cyclopentanol, cyclohexanol, cycloheptanol, cyclooctanol, methylcyclopentanol, ethylcyclopentanol, methylcyclohexanol, ethylcyclohexanol, propylcyclohexanol, butylcyclohexanol, pentylcyclohexanol, hexylcyclohexanol, dimethylcyclohexanol, diethylcyclohexanol, dibutylcyclohexanol, trimethylolbutane, trimethylolpropane, trimethylolethane, pentaerythritol, glycerol, ditrimethylolpropane, dipentaerythritol, sorbitol, mannitol, diglycerol, threitol, erythritol, adonitol (ribitol), arabitol (lyxitol), xylitol and dulcitol (galactitol).

Examples of $R^3$ also include a phenylmethyl group, a phenylethyl group, a phenylpropyl group, a phenylbutyl group, a phenylpentyl group, a phenylhexyl group, a phenylheptyl group, a phenyloctyl group and a phenylnonyl group.

Specific examples of the alcohol having such $R^3$ include phenylmethanol, phenylethanol, phenylpropanol, phenylbutanol, phenylpentanol, phenylhexanol, phenylheptanol, phenyloctanol and phenylnonanol.

Among the above-described alcohols, an alcohol having 1 or 2 alcoholic hydroxy group(s) (hydroxy group(s) forming the hydroxy compound and directly added to a carbon atom not in the aromatic ring) is preferred due to a generally low viscosity, and a monoalcohol having one such alcoholic hydroxy group is more preferred, in terms of industrial use.

Among these, an alkyl alcohol having 1 to 20 carbon atoms is preferred in terms of availability, solubility of the raw material and the product, and the like.

If the hydroxy compound is an aromatic hydroxy compound, the hydroxy compound is a compound represented by the following formula (16):

[Chemical Formula 20]

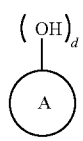

(16)

wherein Ring A represents an organic group containing 6 to 44 carbon atoms which contains an aromatic group substituted with d hydroxy group(s) at any position(s) so that aromaticity is retained, and may be a single ring, a plurality of rings or a heterocycle, or may be substituted with other substituents, and d represents an integer of 1 to 6.

Ring A is preferably a structure containing at least one structure selected from the group consisting of a benzene ring, a naphthalene ring and an anthracene ring. More preferably, Ring A is a structure containing at least one benzene ring. Ring A is also preferably a group having active hydrogen only in the hydroxy group(s).

The hydroxy group bonded to the aromatic group in Ring A is a hydroxy group bonded to a carbon atom of the aromatic group in Ring A. The number of the hydroxy group(s) is 1 to 6, preferably 1 to 3, more preferably 1 to 2, and still more preferably 1 (i.e., d=1).

Specific examples include phenol, methylphenol (each isomer), ethylphenol (each isomer), propylphenol (each isomer), butylphenol (each isomer), pentylphenol (each isomer), hexylphenol (each isomer), octylphenol (each isomer), nonylphenol (each isomer), cumylphenol (each isomer), dimethylphenol (each isomer), methylethylphenol (each isomer), methylpropylphenol (each isomer), methylbutylphenol (each isomer), methylpentylphenol (each isomer), diethylphenol (each isomer), ethylpropylphenol (each isomer), ethylbutylphenol (each isomer), dipropylphenol (each isomer), dicumylphenol (each isomer), trimethylphenol (each isomer), triethylphenol (each isomer) and naphthol (each isomer).

The aromatic hydroxy compound is preferably an aromatic monohydroxy compound having one hydroxyl group directly bonded to the aromatic hydrocarbon ring forming the aromatic hydroxy compound. Although an aromatic hydroxy compound having two or more hydroxyl groups directly bonded to the aromatic hydrocarbon ring forming the aromatic hydroxy compound may be used as such an aromatic hydroxy compound, it is preferred that one hydroxyl group be directly bonded to the aromatic hydrocarbon ring, because the aromatic monohydroxy compound generally has a low viscosity.

The thiol is preferably a compound represented by the following formula (17):

[Chemical Formula 21]

$$R^3 \text{—}(SH)_e \quad (17)$$

wherein $R^3$ represents an aliphatic group having 1 to 44 carbon atoms, or a group having 7 to 44 carbon atoms and composed of an aliphatic group with an aromatic group bonded thereto, which is substituted with e sulfhydryl group(s), the —SH group of the thiol represented by the formula (17) is an —SH group not bonded to the aromatic group, and e represents an integer of 1 to 3, provided that R3 is a group having active hydrogen only in the sulfhydryl group(s).

Examples of $R^3$ include a methyl group, an ethyl group, a propyl group, a butyl group, a pentyl group, a hexyl group, a heptyl group, an octyl group, a nonyl group, a decyl group, a dodecyl group, an octadecyl group, a cyclopentyl group, a cyclohexyl group, a cycloheptyl group, a cyclooctyl group, a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group and a dibutylcyclohexyl group.

Specific examples of the thiol having such $R^3$ include methanethiol, ethanethiol, propanethiol, butanethiol, pentanethiol, hexanethiol, heptanethiol, octanethiol, nonanethiol, decanethiol, dodecanethiol, octadecanethiol, cyclopentanethiol, cyclohexanethiol, cycloheptanethiol, cyclooctanethiol, methylcyclopentanethiol, ethylcyclopentanethiol, methylcyclohexanethiol, ethylcyclohexanethiol, propylcyclohexanethiol, butylcyclohexanethiol, pentylcyclohexanethiol, hexylcyclohexanethiol, dimethylcyclohexanethiol, diethylcyclohexanethiol and dibutylcyclohexanethiol.

Examples of $R^3$ also include a phenylmethyl group, a phenylethyl group, a phenylpropyl group, a phenylbutyl group, a phenylpentyl group, a phenylhexyl group, a phenylheptyl group, a phenyloctyl group and a phenylnonyl group.

Specific examples of the thiol having such $R^3$ include phenylmethanethiol, phenylethanethiol, phenylpropanethiol, phenylbutanethiol, phenylpentanethiol, phenylhexanethiol, phenylheptanethiol, phenyloctanethiol and phenylnonanethiol.

Among the above-described thiols, a thiol having 1 or 2 thiolic sulfhydryl group(s) (sulfhydryl group(s) forming the thiol and directly added to a carbon atom not in the aromatic ring) is preferred due to a generally low viscosity, and a monothiol having one such thiolic sulfhydryl group is more preferred, in terms of industrial use.

Among these, an alkylthiol having 1 to 20 carbon atoms is preferred in terms of availability, solubility of the raw material and the product, and the like.

The aromatic thiol is preferably a compound represented by the following formula (18):

[Chemical Formula 22]

(18)

wherein Ring A represents an organic group containing 6 to 44 carbon atoms which contains an aromatic group substituted with f sulfhydryl group(s) at any position(s) so that aromaticity is retained, and may be a single ring, a plurality of rings or a heterocycle, or may be substituted with other substituents, and f represents an integer of 1 to 6.

Ring A is preferably a structure containing at least one structure selected from the group consisting of a benzene ring, a naphthalene ring and an anthracene ring, and more preferably, Ring A is a structure containing at least one benzene ring. Ring A is also preferably a group having active hydrogen only in the sulfhydryl group(s).

The sulfhydryl group bonded to the aromatic group in Ring A is a sulfhydryl group bonded to a carbon atom of the aromatic group in Ring A. The number of the sulfhydryl group(s) is 1 to 6, preferably 1 to 3, more preferably 1 to 2, and still more preferably 1 (i.e., f=1).

Specific examples include benzenethiol, methylbenzenethiol (each isomer), ethylbenzenethiol (each isomer), propylbenzenethiol (each isomer), butylbenzenethiol (each isomer), pentylbenzenethiol (each isomer), hexylbenzenethiol (each isomer), octylbenzenethiol (each isomer), nonylbenzenethiol (each isomer), cumylbenzenethiol (each isomer), dimethylbenzenethiol (each isomer), methylethylbenzenethiol (each isomer), methylpropylbenzenethiol (each isomer), methylbutylbenzenethiol (each isomer), methylpentylbenzenethiol (each isomer), diethylbenzenethiol (each isomer), ethylpropylbenzenethiol (each isomer), ethylbutylbenzenethiol (each isomer), dipropylbenzenethiol (each isomer), dicumylbenzenethiol (each isomer), trimethylbenzenethiol (each isomer), triethylbenzenethiol (each isomer) and naphthalenethiol (each isomer).

The aromatic thiol is preferably an aromatic monothiol compound having one sulfhydryl group directly bonded to the aromatic hydrocarbon ring forming the aromatic thiol. Although an aromatic thiol having two or more sulfhydryl groups directly bonded to the aromatic hydrocarbon ring forming the aromatic thiol may be used as such an aromatic thiol, an aromatic thiol having 1 or 2 such sulfhydryl groups is preferred because it generally has a low viscosity, and an aromatic monothiol having one such sulfhydryl group is more preferred.

When $X^6$ in the formula (14) is a group represented by the formula (3), R' is an organic group, and the compound represented by the formula (14) containing such an organic group may be a monomer or a polymer. In terms of distillation separation, R' is preferably an organic group having 1 to 44 carbon atoms, and more preferably an alkyl group such as a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), an undecyl group (each isomer) or a dodecyl group (each isomer); a cycloalkyl group such as a cyclopentyl group, a cyclohexyl group, a cycloheptyl group, a cyclooctyl group, a cyclononyl group or a cyclodecyl group; or an aromatic group such as a phenyl group, a methyl-phenyl group (each isomer), an ethyl-phenyl group (each isomer), a propyl-phenyl group (each isomer), a butyl-phenyl group (each isomer), a pentyl-phenyl group (each isomer), a hexyl-phenyl group (each isomer), a heptyl-phenyl group (each isomer), an octyl-phenyl group (each isomer), a nonyl-phenyl group (each isomer), a decyl-phenyl group (each isomer), a dodecyl-phenyl group (each isomer), a phenyl-phenyl group (each isomer), a phenoxy-phenyl group (each isomer), a cumyl-phenyl group (each isomer), a dimethyl-phenyl group (each isomer), a diethyl-phenyl group (each isomer), a dipropyl-phenyl group (each isomer), a dibutyl-phenyl group (each isomer), a dipentyl-phenyl group (each isomer), a dihexyl-phenyl group (each isomer), a diheptyl-phenyl group (each isomer), a diphenyl-phenyl group (each isomer), a diphenoxy-phenyl group (each isomer), a dicumyl-phenyl group (each isomer), a naphthyl group (each isomer) or a methyl-naphthyl group (each isomer).

Examples of the N-substituted carbamic acid ester include N,N'-hexanediyl-bis-carbamic acid diphenyl ester, N,N'-hexanediyl-bis-carbamic acid di(methylphenyl)ester (each isomer), N,N'-hexanediyl-bis-carbamic acid di(ethylphenyl) ester (each isomer), N,N'-hexanediyl-bis-carbamic acid di(propylphenyl)ester (each isomer), N,N'-hexanediyl-bis-carbamic acid di(butylphenyl)ester (each isomer), N,N'-hexanediyl-bis-carbamic acid di(pentylphenyl)ester (each isomer), N,N'-hexanediyl-bis-carbamic acid di(cumylphenyl)ester (each isomer), diphenyl 4,4'-methylene-dicyclohexylcarbamate, di(methylphenyl) 4,4'-methylene-dicyclohexylcarbamate, di(ethylphenyl) 4,4'-methylene-dicyclohexylcarbamate, di(propylphenyl) 4,4'-methylene-dicyclohexylcarbamate (each isomer), di(butylphenyl) 4,4'-methylene-dicyclohexylcarbamate (each isomer), di(pentylphenyl) 4,4'-methylene-dicyclohexylcarbamate (each isomer), di(hexylphenyl) 4,4'-methylene-dicyclohexylcarbamate (each isomer), di(heptylphenyl) 4,4'-methylene-dicyclohexylcarbamate (each isomer), di(cumylphenyl) 4,4'-methylene-dicyclohexylcarbamate (each isomer), 3-(phenoxycarbonylamino-methyl)-3,5,5-trimethylcyclohexylcarbamic acid phenyl ester, 3-(methylphenoxycarbonylamino-methyl)-3,5,5-trimethylcyclohexylcarbamic acid (methylphenoxy) ester (each isomer), 3-(ethylphenoxycarbonylamino-methyl)-3,5,5-trimethylcyclohexylcarbamic acid (ethylphenyl)ester (each isomer), 3-(propylphenoxycarbonylamino-methyl)-3,5,5-trimethylcyclohexylcarbamic acid (propylphenyl)ester (each isomer), 3-(butylphenoxycarbonylamino-methyl)-3,5,5-trimethylcyclohexylcarbamic acid (butylphenyl)ester (each isomer), 3-(pentylphenoxycarbonylamino-methyl)-3,5,5-trimethylcyclohexylcarbamic acid (pentylphenyl)ester (each isomer), 3-(hexylphenoxycarbonylamino-methyl)-3,5,5-trimethylcyclohexylcarbamic acid (hexylphenyl)ester (each isomer), 3-(heptylphenoxycarbonylamino-methyl)-3,5,5-trimethylcyclohexylcarbamic acid (heptylphenyl)ester (each isomer), 3-(cumylphenoxycarbonylamino-methyl)-3,5,5-trimethylcyclohexylcarbamic acid (cumylphenyl)ester (each isomer), toluene-dicarbamic acid diphenyl ester (each isomer), toluene-dicarbamic acid di(methylphenyl)ester (each isomer), toluene-dicarbamic acid di(ethylphenyl)ester (each isomer), toluene-dicarbamic acid di(propylphenyl)ester (each isomer), toluene-dicarbamic acid di(butylphenyl)ester (each isomer), toluene-dicarbamic acid di(pentylphenyl)ester (each isomer), toluene-dicarbamic acid di(hexylphenyl)ester (each isomer), toluene-dicarbamic acid di(heptylphenyl)ester (each isomer), toluene-dicarbamic acid di(octylphenyl)ester (each isomer), N,N'-(4,4'-methanediyl-diphenyl)-biscarbamic acid diphenyl ester, N,N'-(4,4'-methanediyl-diphenyl)-biscarbamic acid di(methylphenyl)ester, N,N'-(4,4'-methanediyl-diphenyl)-biscarbamic acid di(ethylphenyl)ester, N,N'-(4,4'-methanediyl-diphenyl)-biscarbamic acid di(propylphenyl) ester, N,N'-(4,4'-methanediyl-diphenyl)-biscarbamic acid di(butylphenyl)ester, N,N'-(4,4'-methanediyl-diphenyl)-biscarbamic acid di(pentylphenyl)ester, N,N'-(4,4'-methanediyl-diphenyl)-biscarbamic acid di(hexylphenyl)ester, N,N'-(4,4'-methanediyl-diphenyl)-biscarbamic acid di(heptylphenyl)ester and N,N'-(4,4'-methanediyl-diphenyl)-biscarbamic acid di(octylphenyl)ester (each isomer).

The above-described N-substituted carbamic acid esters may be used singly or in a combination of two or more.

Examples of the N-substituted O-substituted thiocarbamic acid ester include N,N'-hexanediyl-bis-thiocarbamic acid di(O-phenyl)ester, N,N'-hexanediyl-bis-thiocarbamic acid di(O-methylphenyl)ester (each isomer), N,N'-hexanediyl-bis-thiocarbamic acid di(O-ethylphenyl)ester (each isomer), N,N'-hexanediyl-bis-thiocarbamic acid di(O-propylphenyl) ester (each isomer), N,N'-hexanediyl-bis-thiocarbamic acid di(O-butylphenyl)ester (each isomer), N,N'-hexanediyl-bis-thiocarbamic acid di(O-pentylphenyl)ester (each isomer), N,N'-hexanediyl-bis-thiocarbamic acid di(O-cumylphenyl)ester (each isomer), di(O-phenyl) 4,4'-methylene-dithiocarbamate, di(O-methylphenyl) 4,4'-methylene-dicyclohexylthiocarbamate, di(O-ethylphenyl) 4,4'-methylene-dicyclohexylthiocarbamate, di(O-propylphenyl) 4,4'-methylene-dicyclohexylthiocarbamate (each isomer), di(O-butylphenyl) 4,4'-methylene-dicyclohexylthiocarbamate (each isomer), di(O-pentylphenyl) 4,4'-methylene-dicyclohexylthiocarbamate (each isomer), di(O-hexylphenyl) 4,4'-methylene-dicyclohexylthiocarbamate (each isomer), di(O-heptylphenyl) 4,4'-methylene-dicyclohexylthiocarbamate (each isomer), di(O-octylphenyl) 4,4'-methylene-dicyclohexylthiocarbamate (each isomer), 3-(phenoxythiocarbonylamino-methyl)-3,5,5-trimethylcyclohexylthiocarbamic acid (O-phenyl)ester, 3-(methylphenoxythiocarbonylamino-methyl)-3,5,5-trimethylcyclohexylthiocarbamic acid (O-methylphenyl)ester (each isomer), 3-(ethylphenoxythiocarbonylamino-methyl)-3,5,5-trimethylcyclohexylthiocarbamic acid (O-ethylphenyl)ester (each isomer), 3-(propylphenoxythiocarbonylamino-methyl)-3,5,5-trimethylcyclohexylcarbamic acid (O-propylphenyl)ester (each isomer), 3-(butylphenoxythiocarbonylamino-methyl)-3,5,5-trimethylcyclohexylthiocarbamic acid (O-butylphenyl)ester (each isomer), 3-(pentylphenoxythiocarbonylamino-methyl)-3,5,5-trimethylcyclohexylthiocarbamic acid (O-pentylphenyl)ester (each isomer), 3-(hexylphenoxythiocarbonylamino-methyl)-3,5,5-trimethylcyclohexylthiocarbamic acid (O-hexylphenyl)ester (each isomer), 3-(heptylphenoxythiocarbonylamino-methyl)-3,5,5-trimethylcyclohexylthiocarbamic acid (O-heptylphenyl) ester (each isomer), 3-(octylphenoxythiocarbonylamino-methyl)-3,5,5-trimethylcyclohexylthiocarbamic acid (O-octylphenyl)ester (each isomer), toluene-bis-thiocarbamic acid di(O-phenyl)ester (each isomer), toluene-bis-thiocarbamic acid di(O-methylphenyl)ester (each isomer), toluene-bis-thiocarbamic acid di(O-ethylphenyl)ester (each isomer), toluene-bis-thiocarbamic acid di(O-propylphenyl) ester (each isomer), toluene-bis-thiocarbamic acid di(O-butylphenyl)ester (each isomer), toluene-bis-thiocarbamic acid di(O-pentylphenyl)ester (each isomer), toluene-bis-thiocarbamic acid di(O-hexylphenyl)ester (each isomer), toluene-bis-carbamic acid di(O-heptylphenyl)ester (each isomer), toluene-bis-thiocarbamic acid di(O-octylphenyl)ester (each isomer), N,N'-(4,4'-methanediyl-diphenyl)-bis-thiocarbamic acid di(O-phenyl)ester, N,N'-(4,4'-methanediyl-diphenyl)-bis-thiocarbamic acid di(O-methylphenyl)ester, N,N'-(4,4'-methanediyl-diphenyl)-bis-thiocarbamic acid di(O-ethylphenyl)ester, N,N'-(4,4'-methanediyl-diphenyl)- bis-thiocarbamic acid di(O-propylphenyl)ester, N,N'-(4,4'-methanediyl-diphenyl)-biscarbamic acid di(butylphenyl)ester, N,N'-(4,4'-methanediyl-diphenyl)-bis-thiocarbamic acid di(O-pentylphenyl)ester, N,N'-(4,4'-methanediyl-diphenyl)-bis-thiocarbamic acid di(O-hexylphenyl)ester, N,N'-(4,4'-methanediyl-diphenyl)-bis-thiocarbamic acid di(O-heptylphenyl)ester and N,N'-(4,4'-methanediyl-diphenyl)-bis-thiocarbamic acid di(O-octylphenyl)ester (each isomer).

The above-described N-substituted O-substituted thiocarbamic acid esters may be used singly or in a combination of two or more.

Examples of the N-substituted S-substituted thiocarbamic acid ester include N,N'-hexanediyl-bis-thiocarbamic acid di(S-phenyl)ester, N,N'-hexanediyl-bis-thiocarbamic acid di(S-methylphenyl)ester (each isomer), N,N'-hexanediyl-bis-thiocarbamic acid di(S-ethylphenyl)ester (each isomer), N,N'-hexanediyl-bis-thiocarbamic acid di(S-propylphenyl)ester (each isomer), N,N'-hexanediyl-bis-thiocarbamic acid di(S-butylphenyl)ester (each isomer), N,N'-hexanediyl-bis-thiocarbamic acid di(S-pentylphenyl)ester (each isomer), di(S-phenyl) 4,4'-methylene-dithiocarbamate, di(S-methylphenyl) 4,4'-methylene-dicyclohexylthiocarbamate, di(S-ethylphenyl) 4,4'-methylene-dicyclohexylthiocarbamate, di(S-propylphenyl) 4,4'-methylene-dicyclohexylthiocarbamate (each isomer), di(S-butylphenyl) 4,4'-methylene-dicyclohexylthiocarbamate (each isomer), di(S-pentylphenyl) 4,4'-methylene-dicyclohexylthiocarbamate (each isomer), di(S-hexylphenyl) 4,4'-methylene-dicyclohexylthiocarbamate (each isomer), di(S-heptylphenyl) 4,4'-methylene-dicyclohexylthiocarbamate (each isomer), di(S-octylphenyl) 4,4'-methylene-dicyclohexylthiocarbamate (each isomer), 3-(phenoxythiocarbonylamino-methyl)-3,5,5-trimethylcyclohexylthiocarbamic acid (S-phenyl)ester, 3-(methylphenoxythiocarbonylamino-methyl)-3,5,5-trimethylcyclohexylthiocarbamic acid (S-methylphenyl)ester (each isomer), 3-(ethylphenoxythiocarbonylamino-methyl)-3,5,5-trimethylcyclohexylthiocarbamic acid (S-ethylphenyl)ester (each isomer), 3-(propylphenoxythiocarbonylamino-methyl)-3,5,5-trimethylcyclohexylcarbamic acid (S-propylphenyl)ester (each isomer), 3-(butylphenoxythiocarbonylamino-methyl)-3,5,5-trimethylcyclohexylthiocarbamic acid (S-butylphenyl)ester (each isomer), 3-(pentylphenoxythiocarbonylamino-methyl)-3,5,5-trimethylcyclohexylthiocarbamic acid (S-pentylphenyl)ester (each isomer), 3-(hexylphenoxythiocarbonylamino-methyl)-3,5,5-trimethylcyclohexylthiocarbamic acid (S-hexylphenyl)ester (each isomer), 3-(heptylphenoxythiocarbonylamino-methyl)-3,5,5-trimethylcyclohexylthiocarbamic acid (S-heptylphenyl)ester (each isomer), 3-(octylphenoxythiocarbonylamino-methyl)-3,5,5-trimethylcyclohexylthiocarbamic acid (S-octylphenyl)ester (each isomer), toluene-bis-thiocarbamic acid di(S-phenyl)ester (each isomer), toluene-bis-thiocarbamic acid di(S-methylphenyl)ester (each isomer), toluene-bis-thiocarbamic acid di(S-ethylphenyl)ester (each isomer), toluene-bis-thiocarbamic acid di(S-propylphenyl)ester (each isomer), toluene-bis-thiocarbamic acid di(S-butylphenyl)ester (each isomer), toluene-bis-thiocarbamic acid di(S-pentylphenyl)ester (each isomer), toluene-bis-thiocarbamic acid di(S-hexylphenyl)ester (each isomer), toluene-bis-carbamic acid di(S-heptylphenyl)ester (each isomer), toluene-bis-carbamic acid di(S-octylphenyl)ester (each isomer), N,N'-(4,4'-methanediyl-diphenyl)-bis-thiocarbamic acid di(S-phenyl)ester, N,N'-(4,4'-methanediyl-diphenyl)-bis-thiocarbamic acid di(S-methylphenyl)ester, N,N'-(4,4'-methanediyl-diphenyl)-bis-thiocarbamic acid di(S-ethylphenyl)ester, N,N'-(4,4'-methanediyl-diphenyl)-bis-thiocarbamic acid di(S-propylphenyl)ester, N,N'-(4,4'-methanediyl-diphenyl)-biscarbamic acid di(butylphenyl)ester, N,N'-(4,4'-methanediyl-diphenyl)-bis-thiocarbamic acid di(S-pentylphenyl)ester, N,N'-(4,4'-methanediyl-diphenyl)-bis-thiocarbamic acid di(S-hexylphenyl)ester, N,N'-(4,4'-methanediyl-diphenyl)-bis-thiocarbamic acid di(S-heptylphenyl)ester and N,N'-(4,4'-methanediyl-diphenyl)-bis-thiocarbamic acid di(S-octylphenyl)ester (each isomer).

The above-described N-substituted S-substituted thiocarbamic acid esters may be used singly or in a combination of two or more.

Examples of the N-substituted dithiocarbamic acid ester include N,N'-hexanediyl-bis-dithiocarbamic acid diphenyl ester, N,N'-hexanediyl-bis-dithiocarbamic acid di(methylphenyl)ester (each isomer), N,N'-hexanediyl-bis-dithiocarbamic acid di(ethylphenyl)ester (each isomer), N,N'-hexanediyl-bis-dithiocarbamic acid di(propylphenyl)ester (each isomer), N,N'-hexanediyl-bis-dithiocarbamic acid di(butylphenyl)ester (each isomer), N,N'-hexanediyl-bis-dithiocarbamic acid di(pentylphenyl)ester (each isomer), diphenyl 4,4'-methylene-didithiocarbamate, di(methylphenyl) 4,4'-methylene-dicyclohexyldithiocarbamate, di(ethylphenyl) 4,4'-methylene-dicyclohexyldithiocarbamate, di(propylphenyl) 4,4'-methylene-dicyclohexyldithiocarbamate (each isomer), di(butylphenyl) 4,4'-methylene-dicyclohexyldithiocarbamate (each isomer), di(pentylphenyl) 4,4'-methylene-dicyclohexyldithiocarbamate (each isomer), di(hexylphenyl) 4,4'-methylene-dicyclohexyldithiocarbamate (each isomer), di(heptylphenyl) 4,4'-methylene-dicyclohexyldithiocarbamate (each isomer), di(octylphenyl) 4,4'-methylene-dicyclohexyldithiocarbamate (each isomer), 3-(phenylsulfonylthiocarbonylamino-methyl)-3,5,5-trimethylcyclohexyldithiocarbamic acid phenyl ester, 3-(methylphenyldithiocarbonylamino-methyl)-3,5,5-trimethylcyclohexyldithiocarbamic acid (methylphenyl)ester (each isomer), 3-(ethylphenyldithiocarbonylamino-methyl)-3,5,5-trimethylcyclohexyldithiocarbamic acid (ethylphenyl)ester (each isomer), 3-(propylphenyldithiocarbonylamino-methyl)-3,5,5-trimethylcyclohexylcarbamic acid (propylphenyl)ester (each isomer), 3-(butylphenyldithiocarbonylamino-methyl)-3,5,5-trimethylcyclohexyldithiocarbamic acid (butylphenyl)ester (each isomer), 3-(pentylphenyldithiocarbonylamino-methyl)-3,5,5-trimethylcyclohexyldithiocarbamic acid (pentylphenyl)ester (each isomer), 3-(hexylphenyldithiocarbonylamino-methyl)-3,5,5-trimethylcyclohexyldithiocarbamic acid (hexylphenyl)ester (each isomer), 3-(heptylphenyldithiocarbonylamino-methyl)-3,5,5-trimethylcyclohexyldithiocarbamic acid (heptylphenyl)ester (each isomer), 3-(octylphenyldithiocarbonylamino-methyl)-3,5,5-trimethylcyclohexyldithiocarbamic acid (octylphenyl)ester (each isomer), toluene-bis-dithiocarbamic acid diphenyl ester (each isomer), toluene-bis-dithiocarbamic acid di(methylphenyl)ester (each isomer), toluene-bis-dithiocarbamic acid di(ethylphenyl)ester (each isomer), toluene-bis-dithiocarbamic acid di(propylphenyl)ester (each isomer), toluene-bis-dithiocarbamic acid di(butylphenyl)ester (each isomer), toluene-bis-dithiocarbamic acid di(pentylphenyl)ester (each isomer), toluene-bis-dithiocarbamic acid di(hexylphenyl)ester (each isomer), toluene-bis-carbamic acid di(heptylphenyl)ester (each isomer), toluene-bis-carbamic acid di(octylphenyl)ester (each isomer), N,N'-(4,4'-methanediyl-diphenyl)-bis-dithiocarbamic acid diphenyl ester, N,N'-(4,4'-methanediyl-diphenyl)-bis-dithiocarbamic acid di(methylphenyl)ester, N,N'-(4,4'-methanediyl-diphenyl)-bis-dithiocarbamic acid di(ethylphenyl)ester, N,N'-(4,4'-methanediyl-diphenyl)-bis-dithiocarbamic acid di(propylphenyl)ester, N,N'-(4,4'-methanediyl-diphenyl)-biscarbamic acid di(butylphenyl)ester, N,N'-(4,4'-methanediyl-diphenyl)-bis-dithiocarbamic acid di(pentylphenyl)ester, N,N'-(4,4'-methanediyl-diphenyl)-bis-dithiocarbamic acid di(hexylphenyl)ester, N,N'-(4,4'-methanediyl-diphenyl)-bis-dithiocarbamic acid di(heptylphenyl)ester and N,N'-(4,4'-methanediyl-diphenyl)-bis-dithiocarbamic acid di(octylphenyl)ester (each isomer).

The above-described N-substituted dithiocarbamic acid esters may be used singly or in a combination of two or more.

The methods for producing the N-substituted carbamic acid ester, N-substituted O-substituted thiocarbamic acid ester, N-substituted S-substituted thiocarbamic acid ester and N-substituted dithiocarbamic acid ester are not particularly limited and various known methods can be used.

When $X^6$ is a group represented by the formula (4), the compound represented by the formula (14) is an N-substituted ureido (if $X^4$ is an oxygen atom) or an N-substituted thioureido (if $X^4$ is a sulfur atom).

Examples of the N-substituted ureido include N-phenylurea, N-(methylphenyl)urea (each isomer), N-(dimethylphenyl)urea (each isomer), N-(diethylphenyl)urea (each isomer), N-(dipropylphenyl)urea (each isomer), N-naphthylurea (each isomer), N-(methylnaphthyl)urea (each isomer), N-dimethylnaphthylurea (each isomer), N-trimethylnaphthylurea (each isomer), N-aliphatic diureas such as N,N'-phenylenediurea (each isomer), N,N'-methylphenylenediurea (each isomer), N,N'-methylenediphenylenediurea (each isomer), N,N'-mesitylenediurea (each isomer), N,N'-biphenylenediurea (each isomer), N,N'-diphenylenediurea (each isomer), N,N'-propylenediphenylenediurea (each isomer), N,N'-oxy-diphenylenediurea (each isomer), bis(ureidophenoxyethane) (each isomer), N,N'-xylenediurea (each isomer), N,N'-methoxyphenyldiurea (each isomer), N,N'-ethoxyphenyldiurea (each isomer), N,N'-naphthalenediurea (each isomer), N,N'-methylnaphthalenediurea (each isomer), N,N'-ethylenediurea, N,N'-propylenediurea (each isomer), N,N'-butylenediurea (each isomer), N,N'-pentamethylenediurea (each isomer), N,N'-hexanemethylenediurea (each isomer) and N,N'-decamethylenediurea (each isomer); N-aliphatic triureas such as N,N',N''-hexamethylenetriurea (each isomer), N,N',N''-nonamethylenetriurea (each isomer) and N,N',N''-decamethylenetriurea (each isomer); and substituted N-cyclic aliphatic polyureas such as N,N'-cyclobutylenediurea (each isomer), N,N'-methylenedicyclohexyldiurea (each isomer), 3-ureidomethyl-3,5,5-trimethylcyclohexylurea (cis and/or trans forms) and methylenebis(cyclohexylurea) (each isomer).

Examples of the N-substituted thioureido include N-phenylthiourea, N-(methylphenyl)thiourea (each isomer), N-(dimethylphenyl)thiourea (each isomer), N-(diethylphenyl)thiourea (each isomer), N-(dipropylphenyl)thiourea (each isomer), N-naphthylthiourea (each isomer), N-(methylnaphthyl)thiourea (each isomer), N-dimethylnaphthylthiourea (each isomer), N-trimethylnaphthylthiourea (each isomer), N-aliphatic dithioureas such as N,N'-phenylenedithiourea (each isomer), N,N'-methylphenylenedithiourea (each isomer), N,N'-methylenediphenylenedithiourea (each isomer), N,N'-mesitylenedithiourea (each isomer), N,N'-biphenylenedithiourea (each isomer), N,N'-diphenylenedithiourea (each isomer), N,N'-propylenediphenylenedithiourea (each isomer), N,N'-oxy-diphenylenedithiourea (each isomer), bis(thioureidophenoxyethane) (each isomer), N,N'-xylenedithiourea (each isomer), N,N'-methoxyphenyldithiourea (each isomer), N,N'-ethoxyphenyldithiourea (each isomer), N,N'-naphthalenedithiourea (each isomer), N,N'-methylnaphthalenedithiourea (each isomer), N,N'-ethylenedithiourea, N,N'-propylenedithiourea (each isomer), N,N'-butylenedithiourea (each isomer), N,N'-pentamethylenedithiourea (each isomer), N,N'-hexanemethylenedithiourea (each isomer) and N,N'-decamethylenedithiourea (each isomer); N-aliphatic trithioureas such as N,N',N''-hexamethylenetrithiourea (each isomer), N,N',N''-nonamethylenetrithiourea (each isomer) and N,N',N''-decamethylenetrithiourea (each isomer); and substituted N-cyclic aliphatic polythioureas such as N,N'-cyclobutylenedithiourea (each isomer), N,N'-methylenedicyclohexyldithiourea (each isomer), 3-thioureidomethyl-3,5,5-trimethylcyclohexylthiourea (cis and/or trans forms) and methylenebis(cyclohexylthiourea) (each isomer).

Examples of the compound having a hydrogen atom bonded to a halogen atom include hydrogen chloride, hydrogen bromide and hydrogen iodide.

Examples of (B) include compounds having a carbonyl group (>C=O). Examples of the compounds having a carbonyl group include compounds having at least one group selected from the group consisting of groups represented by the following formulas (5) to (8):

[Chemical Formula 23]

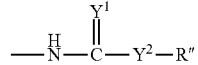
(5)

[Chemical Formula 24]

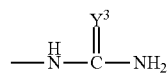
(6)

[Chemical Formula 25]

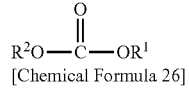
(7)

[Chemical Formula 26]

(8)

wherein $Y^1$, $Y^2$, $Y^3$ and $Y^4$ ($Y^1$ to $Y^4$) each independently represent an oxygen atom or a sulfur atom, $R^1$ and $R^2$ each independently represent an organic group having 1 to 30 carbon atoms, and R'' represents an organic group.

The formula (7) is a carbonic acid ester. Examples of the compounds having groups represented by the formulas (5), (6) and (8) include compounds represented by the following formula (19):

[Chemical Formula 27]

(19)

wherein $R^4$ represents an organic group having 1 to 80 carbon atoms, $Y^6$ represents at least one group selected from the group consisting of groups represented by the formulas (5), (6) and (8), and b represents an integer of 1 to 10.

Examples of $R^4$ in the formula (19) include an aliphatic group, an aromatic group, or a group prepared by bonding an aliphatic group and an aromatic group to each other. More specific examples include an acyclic hydrocarbon group, a cyclic hydrocarbon group (e.g., a monocyclic hydrocarbon group, a fused polycyclic hydrocarbon group, a crosslinked cyclic hydrocarbon group, a spiro hydrocarbon group, a ring assembly hydrocarbon group, a cyclic hydrocarbon group with a side chain, a heterocyclic group, a heterocyclic spiro group, a hetero crosslinked ring group or a heterocyclic group), a group in which one or more groups selected from the group consisting of the acyclic hydrocarbon groups and the cyclic hydrocarbon groups are bonded to each other, or a group in which one or more groups selected from the above-described group are bonded to each other via a covalent bond with a specific non-metal atom (carbon, oxygen, nitrogen, sulfur or silicon).

$R^4$ is particularly preferably a group selected from an aliphatic group, an aromatic group, and a group prepared by bonding an aliphatic group and an aromatic group to each other and having 1 to 80 carbon atoms, because a side reaction is less likely to occur, and preferably a group having 1 to 70 carbon atoms, and more preferably a group having 1 to 30 carbon atoms, taking fluidity and the like into consideration.

Examples of $R^4$ include linear hydrocarbon groups such as methylene, dimethylene, trimethylene, tetramethylene, pentamethylene, hexamethylene and octamethylene; groups derived from unsubstituted alicyclic hydrocarbons such as cyclopentane, cyclohexane, cycloheptane, cyclooctane and bis(cyclohexyl)alkane; groups derived from alkyl-substituted cyclohexanes such as methylcyclopentane, ethylcyclopentane, methylcyclohexane (each isomer), ethylcyclohexane (each isomer), propylcyclohexane (each isomer), butylcyclohexane (each isomer), pentylcyclohexane (each isomer) and hexylcyclohexane (each isomer); groups derived from dialkyl-substituted cyclohexanes such as dimethylcyclohexane (each isomer), diethylcyclohexane (each isomer) and dibutylcyclohexane (each isomer); groups derived from trialkyl-substituted cyclohexanes such as 1,5,5-trimethylcyclohexane, 1,5,5-triethylcyclohexane, 1,5,5-tripropylcyclohexane (each isomer) and 1,5,5-tributylcyclohexane (each isomer); groups derived from monoalkyl-substituted benzenes such as toluene, ethylbenzene and propylbenzene; groups derived from dialkyl-substituted benzenes such as xylene, diethylbenzene and dipropylbenzene; and groups derived from aromatic hydrocarbons such as diphenylalkane and benzene. Particular examples include groups derived from hexamethylene, phenylene, diphenylmethane, toluene, cyclohexane, xylenyl, methylcyclohexane, isophorone and dicyclohexylmethane.

When $Y^6$ is a group represented by the formula (5), the compound represented by the formula (19) is an N-substituted carbamic acid ester (if $Y^1$ and $Y^2$ are oxygen atoms), an N-substituted O-substituted thiocarbamic acid ester (if $Y^1$ is a sulfur atom and $Y^2$ is an oxygen atom), an N-substituted S-substituted thiocarbamic acid ester (if $Y^1$ is an oxygen atom and $Y^2$ is a sulfur atom) or an N-substituted dithiocarbamic acid ester (if $Y^1$ and $Y^2$ are sulfur atoms). Preferred examples of these compounds are as described above (R" is similar to R'). When $Y^6$ is a group represented by the formula (6), the compound represented by the formula (19) is an N-substituted ureido (if $Y^3$ is an oxygen atom) or an N-substituted thioureido (if $Y^3$ is a sulfur atom). Preferred examples of these compounds are as described above. When $Y^6$ is a group represented by the formula (8), the compound represented by the formula (19) is an isocyanate (if $Y^4$ is an oxygen atom) or an isothiocyanate (if $Y^4$ is a sulfur atom).

The carbonic acid ester refers to a compound in which one or two of the two hydrogen atoms in carbonic acid $CO(OH)_2$ are each replaced with an aliphatic group or an aromatic group.

Examples of the aliphatic group represented by $R^1$ and $R^2$ in the formula (7) include groups formed by specific non-metal atoms (carbon, oxygen, nitrogen, sulfur, silicon and halogen atoms). Preferred examples of the aliphatic group include a chain hydrocarbon group, a cyclic hydrocarbon group, and a group in which one or more groups selected from the group consisting of the chain hydrocarbon groups and the cyclic hydrocarbon groups are bonded to each other (e.g., a cyclic hydrocarbon group substituted with a chain hydrocarbon group, or a chain hydrocarbon group substituted with a cyclic hydrocarbon group). Examples of the aralkyl group include a group in which a linear and/or branched alkyl group is substituted with an aromatic group. Preferred examples of the aromatic group include groups formed by specific non-metal atoms (carbon, oxygen, nitrogen, sulfur, silicon and halogen atoms) as described above, specifically, a monocyclic aromatic group, a fused polycyclic aromatic group, a crosslinked cyclic aromatic group, a ring assembly aromatic group and a heterocyclic aromatic group. More preferred examples include a substituted and/or unsubstituted phenyl group, a substituted and/or unsubstituted naphthyl group, and a substituted and/or unsubstituted anthryl group.

Examples of the aromatic group represented by $R^1$ and $R^2$ include groups formed by specific non-metal atoms (carbon, oxygen, nitrogen, sulfur, silicon and halogen atoms), specifically, a monocyclic aromatic group, a fused polycyclic aromatic group, a crosslinked cyclic aromatic group, a ring assembly aromatic group and a heterocyclic aromatic group. More preferred examples include a substituted and/or unsubstituted phenyl group, a substituted and/or unsubstituted naphthyl group, and a substituted and/or unsubstituted anthryl group. The substituent may be a hydrogen atom, an aliphatic group (referring to a chain hydrocarbon group, a cyclic hydrocarbon group, and a group in which one or more groups selected from the chain hydrocarbon groups and the cyclic hydrocarbon groups are bonded to each other (e.g., a cyclic hydrocarbon group substituted with a chain hydrocarbon group, or a chain hydrocarbon group substituted with a cyclic hydrocarbon group)), or an aromatic group as described above, or may be a group formed by the aliphatic group and the aromatic group.

Examples of such $R^1$ and $R^2$ include alkyl groups such as a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), an undecyl group (each isomer), a dodecyl group (each isomer), a tridecyl group (each isomer), a tetradecyl group (each isomer), a pentadecyl group (each isomer), a hexadecyl group (each isomer), a heptadecyl group (each isomer), an octadecyl group (each isomer), a nonadecyl group (each isomer) and an eicosyl group (each isomer); aryl groups such as a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a heptylphenyl group (each isomer), an octylphenyl group (each isomer), a nonylphenyl group (each isomer), a decylphenyl group (each isomer), a biphenyl group (each isomer), a dimethylphenyl group (each isomer), a diethylphenyl group (each isomer), a dipropylphenyl group (each isomer), a dibutylphenyl group (each isomer), a dipentylphenyl group (each isomer), a dihexylphenyl group (each isomer), a diheptylphenyl group (each isomer), a terphenyl group (each isomer), a trimethylphenyl group (each isomer), a triethylphenyl group (each isomer), a tripropylphenyl group (each isomer) and a tributylphenyl group (each isomer); and aralkyl groups such as a phenylmethyl group, a phenylethyl group (each isomer), a phenylpropyl group (each isomer), a phenylbutyl group (each isomer), a phenylpentyl group (each isomer), a phenylhexyl group (each isomer), a phenylheptyl group (each isomer), a phenyloctyl group (each isomer) and a phenylnonyl group (each isomer). Among these carbonic acid esters, dimethyl carbonate, diethyl carbonate, dipropyl carbonate (each isomer), dibutyl carbonate (each isomer), dipentyl carbonate (each isomer), dihexyl carbonate (each isomer), diheptyl carbonate (each isomer), dioctyl carbonate (each isomer), diphenyl carbonate, methylphenyl carbonate and the like are preferred.

Examples of the compounds having a group represented by the formula (8) include compounds represented by the following formula (10). The compounds are preferably used in the separation method of the present embodiment.

[Chemical Formula 28]

(10)

In the formula, $R^4$ represents an organic group having 1 to 80 carbon atoms, $Y^5$ represents an oxygen atom or a sulfur atom, and b represents an integer of 1 to 10.

When $Y^5$ is an oxygen atom, the compound represented by the formula (10) is an isocyanate. When $Y^5$ is a sulfur atom, the compound represented by the formula (10) is an isothiocyanate.

First, the isocyanate will be described. The isocyanate in the present embodiment is a compound corresponding to "its hydrocarbyl derivatives: RN=C=O" in the latter half of "The isocyanic acid tautomer, HN=C=O, of cyanic acid, HOC=N and its hydrocarbyl derivatives: RN=C=O" in the paragraph for "isocyanates" defined in Rule C-8 described in the Nomenclature (IUPAC Nomenclature of Organic Chemistry) established by the IUPAC (The International Union of Pure and Applied Chemistry). It is preferably a compound represented by the following formula (20):

[Chemical Formula 29]

(20)

wherein $R^4$ represents an organic group having 1 to 80 carbon atoms, and b represents an integer of 1 to 10.

In the formula (20), $R^4$ is preferably one group selected from the group consisting of an aliphatic group having 1 to 22 carbon atoms and an aromatic group having 6 to 22 carbon atoms. The group may contain an oxygen atom or a nitrogen atom. Preferred examples of $R^4$ include linear hydrocarbon groups such as methylene, dimethylene, trimethylene, tetramethylene, pentamethylene, hexamethylene and octamethylene; groups derived from unsubstituted alicyclic hydrocarbons such as cyclopentane, cyclohexane, cycloheptane, cyclooctane and bis(cyclohexyl)alkane; groups derived from alkyl-substituted cyclohexanes such as methylcyclopentane, ethylcyclopentane, methylcyclohexane (each isomer), ethylcyclohexane (each isomer), propylcyclohexane (each isomer), butylcyclohexane (each isomer), pentylcyclohexane (each isomer) and hexylcyclohexane (each isomer); groups derived from dialkyl-substituted cyclohexanes such as dimethylcyclohexane (each isomer), diethylcyclohexane (each isomer) and dibutylcyclohexane (each isomer); groups derived from trialkyl-substituted cyclohexanes such as 1,5,5-trimethylcyclohexane, 1,5,5-triethylcyclohexane, 1,5,5-tripropylcyclohexane (each isomer) and 1,5,5-tributylcyclohexane (each isomer); monoalkyl-substituted benzenes such as toluene, ethylbenzene and propylbenzene; dialkyl-substituted benzenes such as xylene, diethylbenzene and dipropylbenzene; and groups derived from aromatic hydrocarbons such as diphenylalkane and benzene. Particularly preferred examples include groups derived from hexamethylene, phenylene, diphenylmethane, toluene, cyclohexane, xylenyl, methylcyclohexane, isophorone and dicyclohexylmethane.

In the formula (20), preferred b is an integer of 1 to 3, and a diisocyanate where b is 2 is more preferred.

Specific examples of preferred isocyanates include phenyl isocyanate, naphthalene isocyanate, hexamethylene diisocyanate, isophorone diisocyanate, diphenylmethane diisocyanate (each isomer), tolylene diisocyanate (each isomer), methylenebis(cyclohexane) diisocyanate, naphthalene diisocyanate (each isomer), triisocyanates, e.g., triisocyanatononane, 2,4,6-triisocyanatotoluene, triphenylmethane triisocyanate or 2,4,4'-triisocyanatodiphenyl ether, or a mixture made of di-, tri- and higher polyisocyanates. Examples of the polyisocyanates include polyphenyl polyisocyanates obtained by phosgenation of a corresponding aniline/formaldehyde condensate and having a methylene bridge.

Next, the isothiocyanate will be described. The isothiocyanate in the present embodiment is "sulfur analogues of isocyanates: RN=C=S" in the paragraph for "isothiocyanates" defined in Rule C-8 described in the Nomenclature (IUPAC Nomenclature of Organic Chemistry) established by the IUPAC (The International Union of Pure and Applied Chemistry). It is preferably a compound represented by the following formula (21):

[Chemical Formula 30]

(21)

wherein $R^4$ represents an organic group having 1 to 80 carbon atoms, and b represents an integer of 1 to 10.

Preferred $R^4$ in the formula (21) is similar to $R^4$ in the formula (20).

In the formula (21), preferred b is an integer of 1 to 3, and a diisothiocyanate where b is 2 is more preferred.

Specific examples of preferred isothiocyanates include phenyl isothiocyanate, naphthalene isothiocyanate, hexamethylene diisothiocyanate, isophorone diisothiocyanate, diphenylmethane diisothiocyanate (each isomer), tolylene diisothiocyanate (each isomer), methylenebis(cyclohexane) diisothiocyanate, naphthalene diisothiocyanate (each isomer) and lysine diisothiocyanate.

In an embodiment, the separation method of the present invention can be used in producing an allophanate group-containing polyisocyanate.

Examples of the allophanate group-containing polyisocyanate include compounds represented by the following formula (22):

[Chemical Formula 31]

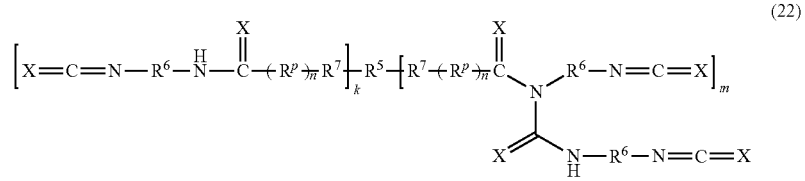

(22)

wherein
$R^5$ represents a (k+m)-valent organic group,
$R^6$s each independently represent a group derived from an isocyanate,
$R^7$ represents an oxygen atom or a nitrogen atom,
$R^p$ represents a group selected from the group consisting of —CH$_2$—CH$_2$—O—, —CH$_2$—CH(CH$_3$)—O—, —CH(CH$_3$)—CH$_2$—O—, —CH$_2$—C(CH$_3$)$_2$—O—, —C(CH$_3$)$_2$—CH$_2$—O—, —CH$_2$—CH(Vin)-O—, —CH(Vin)-CH$_2$—O—, —CH$_2$—CHPh-O—, —CHPh-CH$_2$—O—, —CH$_2$—CH$_2$—S—, —CH$_2$—CH(CH$_3$)—S—, —CH(CH$_3$)—CH$_2$—S—, —CH$_2$—C(CH$_3$)$_2$—S—, —C(CH$_3$)$_2$—CH$_2$—S—, —CH$_2$—CH(Vin)-S—, —CH(Vin)-CH$_2$—S—, —CH$_2$—CHPh-S— and —CHPh-CH$_2$—S-(where Ph represents a phenyl group and Vin represents a vinyl group), and a plurality of $R^p$s may be respectively identical or different from each other,
X represents an oxygen atom or a sulfur atom,
k represents 0 or a positive number,
m represents a positive number,
k+m is a number of 3 or more, and
n represents 0 or a positive number.

In the formula (22), m>k is preferred, and m≥(k+1) is more preferred. k≤0.5 is preferred, k≤0.2 is more preferred, and k=0 is still more preferred.

$R^5$ in the formula (22) may be a group derived from a hydroxy compound or a thiol (including an aromatic thiol), for example. Specifically, it may be a residue in which (k+m) —OH groups are excluded from a hydroxy compound, or a residue in which (k+m) —SH groups are excluded from a thiol (including an aromatic thiol), for example. The (k+m) value is preferably a number of 3 or more, more preferably a number of 3 to 6, still more preferably a number of 3 to 4, and even more preferably 3. When the hydroxy compound is an alcohol represented by the formula (15), c in the formula (15) is a number of (k+m) or more. This also applies to an aromatic hydroxy compound represented by the formula (16), a thiol represented by the formula (17) and an aromatic thiol represented by the formula (18).

$R^5[-R^7-(R^p)_n-H]_{(k+m)}$ in the formula (22) may be a group derived from a hydroxy compound or a thiol (including an aromatic thiol). Examples of the hydroxy compound in this case include triethanolamine, tripropanolamine and 1,3,5-tris(2-hydroxyethyl)cyanuric acid.

$R^6$ in the formula (22) may be a group derived from an isocyanate or isothiocyanate, for example. In the case of an isocyanate represented by the formula (20), $R^6$ corresponds to $R^4$ in the formula (20), and in the case of an isothiocyanate represented by the formula (21), $R^6$ corresponds to $R^4$ in the formula (21). A diisocyanate of the formula (20) where a is 2, or a diisothiocyanate of the formula (21) where b is 2, is preferred.

The number average molecular weight Mn of the allophanate group-containing polyisocyanate represented by the formula (22) is usually less than 2000 g/mol, preferably less than 1800 g/mol, more preferably less than 1500 g/mol, still more preferably less than 1200 g/mol, and particularly preferably less than 1100 g/mol. The lower limit of the number average molecular weight Mn is not particularly limited, but is usually 250 g/mol or more. The number average molecular weight Mn is a value measured by gel permeation chromatography (GPC) with polystyrene as the standard.

The content of the NCX group (NCO or NCS group) in the formula (22) is usually higher than 5 mass %, preferably higher than 6 mass %, and more preferably higher than 8 mass % and up to 17 mass %, preferably up to 15 mass %.

The allophanate group-containing polyisocyanate in the present embodiment may contain, in addition to the allophanate group, other reactive groups such as unreacted hydroxy, sulfhydryl and isocyanurate groups without departing from the spirit of the present embodiment.

The allophanate group-containing polyisocyanate can be produced by reacting the isocyanate and/or isothiocyanate with a hydroxy compound and/or thiol (including an aromatic thiol), for example. The reaction conditions will be described below.

The reaction temperature is usually up to 150° C., preferably up to 120° C., more preferably less than 100° C., and still more preferably less than 90° C. The reaction is preferably performed in the presence of at least one catalyst catalyzing urethanation reaction and/or allophanation reaction. However, the urethane group may also be formed in the absence of a catalyst.

Here, the catalyst is a compound in which the presence of the catalyst in the starting material allows a urethane group or allophanate group-containing polyisocyanate to be generated in an amount larger than the case where the same starting material is used under the same reaction conditions without the catalyst.

Examples of the catalyst include organic amines, in particular, tertiary aliphatic, alicyclic or aromatic amines, and/or organometallic compounds of Lewis acids. Examples of the organometallic compounds of Lewis acids include tin compounds, specifically, tin(II) salts of organic carboxylic acids such as tin(II) diacetate, tin(II) dioctoate, tin(II) bis(ethylhexanoate) and tin(II) dilaurate; and dialkyltin(IV) salts of organic carboxylic acids such as dimethyltin diacetate, dibutyltin diacetate, dibutyltin dibutyrate, dibutyltin bis(2-ethylhexanoate), dibutyltin dilaurate, dibutyltin maleate, dioctyltin dilaurate and dioctyltin diacetate. Zinc (II) salts (e.g., zinc(II) dioctoate) may also be used. Acetylacetonates of metal complexes (e.g., iron, titanium, aluminum, zirconium, manganese, nickel, zinc and cobalt) may further be used.

Dimethyltin diacetate, dibutyltin dibutyrate, dibutyltin bis(2-ethylhexanoate), dibutyltin dilaurate, dioctyltin dilaurate, zinc(II) dioctoate, zirconium acetylacetonate and zirconium 2,2,6,6-tetramethyl-3,5-heptanedionate are preferred as organometallic compounds of Lewis acids.

The amount of the catalyst used is 0.001 to 10 mol %, preferably 0.5 to 8 mol %, more preferably 1 to 7 mol %, and still more preferably 2 to 5 mol % based on the NCX group (NCO group and/or NCS group).

The reaction time is not particularly limited, but is preferably 0.001 to 50 hours, more preferably 0.01 to 20 hours, and still more preferably 0.1 to 10 hours. The reaction can also be completed after collecting the reaction solution and confirming that an allophanate group-containing polyisocyanate having a desired number average molecular weight has been generated, using gel permeation chromatography, for example.

The reaction is preferably performed without a solvent, but a solvent may be used in order to lower the viscosity to ensure fluidity, for example.

The solvent is preferably a solvent which is inert to an isocyanate or isothiocyanate group and in which a polyisocyanate is dissolved preferably at 10 mass % or more, more preferably at 25 mass % or more, still more preferably at 50 mass % or more, and even more preferably at 75 mass % or more.

Aromatic hydrocarbons (including alkylated benzenes and naphthalenes) and/or (cyclic) aliphatic hydrocarbons, and mixtures thereof, chlorinated hydrocarbons, ketones, esters, alkoxylated alkanoic acid alkyl esters, ethers, and mixtures of these solvents can be used as such solvents.

The aromatic hydrocarbons and mixtures thereof are preferably compounds having a boiling point range of 80 to 350° C. and having 7 to carbon atoms. Specifically, toluene, o-, m- or p-xylene, trimethylbenzene isomers, tetramethylbenzene isomers, ethylbenzene, cumene, tetrahydronaphthalene, and mixtures containing these are preferred. Examples include Solvesso® of Exxon Mobil Chemical, in particular, Solvesso® 100 (CAS No. 64742-95-6, mainly C9-C10 aromatic compounds, boiling point range ca. 154 to 178° C.), 150 (boiling point range ca. 182 to 207° C.) and 200 (CAS No. 64742-94-5), as well as Shellsol® of Shell, Caromax® of Petrochem Carless (e.g., Caromax® 18) and Hydrosol of DHC (e.g., Hydrosol® A170). Hydrocarbon mixtures composed of paraffins, cycloparaffins and aromatic compounds include trade name Kristalloel (e.g., Kristalloel 30, boiling point range ca. 158 to 198° C. or Kristalloel 60: CAS No. 64742-82-1), white spirit (e.g., similarly, CAS No. 64742-82-1) or solvent naphtha (light: boiling point range ca. 155 to 180° C., heavy: boiling point range ca. 225 to 300° C.). The content of the aromatic compound in such a hydrocarbon mixture is generally higher than 90 mass %, preferably higher than 95 mass %, particularly preferably higher than 98 mass %, and still particularly preferably higher than 99 mass %. It may be advantageous to use a hydrocarbon mixture having a particularly low naphthalene content.

Examples of the (cyclic) aliphatic hydrocarbons include decalin, alkylated decalin, and isomer mixtures of linear or branched alkanes and/or cycloalkanes.

Examples of the esters include n-butyl acetate, ethyl acetate, 1-methoxypropyl acetate and 2-methoxyethyl acetate.

Examples of the ethers include THF, dioxane, and ethylene glycol, diethylene glycol, triethylene glycol, propylene glycol, dipropylene glycol or tripropylene glycol dimethyl ether, diethyl ether or n-butyl ether.

Examples of the ketones include acetone, diethyl ketone, ethyl methyl ketone, isobutyl methyl ketone, methyl amyl ketone and t-butyl methyl ketone.

Polyisocyanates are compounds having at least one component (binder) containing a group reactive to an isocyanate and/or an isothiocyanate, and are useful in two-component polyurethane paints. Such polyisocyanates can be obtained by oligomerization of monomer isocyanates, for example.

The monomer isocyanates and/or isothiocyanates used may be aromatic, aliphatic or alicyclic, and are preferably aliphatic or alicyclic (herein briefly called (cyclic) aliphatic), more preferably aliphatic isocyanates and/or aliphatic isothiocyanates, and still more preferably aliphatic isocyanates.

Reaction mixtures containing the allophanate group-containing polyisocyanates produced by the method described above contain unreacted isocyanates, isothiocyanates, hydroxy compounds and thiols (including aromatic thiols). Although these unreacted products may be allowed to remain in the reaction mixtures, the allophanate group-containing polyisocyanates are suitably used as urethane paints in applications requiring appearance quality such as automotive paints and construction paints, and it is thus preferred to remove the unreacted products from the reaction mixtures, and the separation method of the present embodiment is suitably used.

In an embodiment, the separation method of the present invention can also be suitably used in distillation separation of a mixture obtained by thermal decomposition reaction of the above-described N-substituted carbamic acid ester, N-substituted O-substituted thiocarbamic acid ester, N-substituted S-substituted thiocarbamic acid ester or N-substituted dithiocarbamic acid ester.

The methods for producing such an N-substituted carbamic acid ester, N-substituted O-substituted thiocarbamic acid ester, N-substituted S-substituted thiocarbamic acid ester and N-substituted dithiocarbamic acid ester are not particularly limited and various known methods can be used. Such an N-substituted carbamic acid ester, N-substituted O-substituted thiocarbamic acid ester, N-substituted S-substituted thiocarbamic acid ester and N-substituted dithiocarbamic acid ester may be a single ester or a mixture of a plurality of esters.

Since the N-substituted carbamic acid ester, the N-substituted O-substituted thiocarbamic acid ester, the N-substituted S-substituted thiocarbamic acid ester and the N-substituted dithiocarbamic acid ester are all subjected to a similar operation for thermal decomposition reaction, the thermal decomposition reaction for these above-described compounds will be described below using thermal decomposition reaction of the N-substituted carbamic acid ester as an example. An isocyanate and a hydroxy compound are generated in thermal decomposition reaction of the N-substituted carbamic acid ester, and the isocyanate may be replaced with a corresponding isothiocyanate for thermal decomposition reaction of the N-substituted O-substituted thiocarbamic acid ester, the hydroxy compound may be replaced with a corresponding thiol or aromatic thiol for thermal decomposition reaction of the N-substituted S-substituted thiocarbamic acid ester and the isocyanate may be replaced with a corresponding isothiocyanate and the hydroxy compound may be replaced with a corresponding thiol or aromatic thiol for thermal decomposition reaction of the N-substituted dithiocarbamic acid ester.

The step of producing a mixture containing an isocyanate and a hydroxy compound by subjecting the N-substituted carbamic acid ester to thermal decomposition reaction.

This step may be performed with or without a solvent, but is preferably implemented in the presence of a hydroxy compound. When a hydroxy compound is used in the production of the N-substituted carbamic acid ester, the hydroxy compound can be directly used as a hydroxy compound in this step. In the case of a method of producing the N-substituted carbamic acid ester by reaction of a carbonic acid ester with an organic primary amine, since a hydroxy compound is generated as a reaction by-product, the hydroxy compound can be directly used as a hydroxy compound in this step. If necessary, this step may be implemented after adjusting the amount of the hydroxy compound.

The number of moles of the hydroxy compound is preferably 0.2 to 50 times, more preferably 0.3 to 30 times, and still more preferably 1 to 20 times of the total number of moles of the ester groups contained in the N-substituted carbamic acid ester in terms of the transfer efficiency of the N-substituted carbamic acid ester and the size of the storage tank during storage.

An appropriate inert solvent may be added in order to make the reaction operation easier, for example. Examples of the inert solvent include alkanes such as hexane (each isomer), heptane (each isomer), octane (each isomer), nonane (each isomer) and decane (each isomer); aromatic hydrocarbons and alkyl-substituted aromatic hydrocarbons such as benzene, toluene, xylene (each isomer), ethylbenzene, diisopropylbenzene (each isomer), dibutylbenzene (each isomer) and naphthalene; aromatic compounds substituted with a halogen or nitro group such as chlorobenzene, dichlorobenzene (each isomer), bromobenzene, dibromobenzene (each isomer), chloronaphthalene, bromonaphthalene, nitrobenzene and nitronaphthalene; polycyclic hydrocarbon compounds such as diphenyl, substituted diphenyl, diphenylmethane, terphenyl, anthracene and dibenzyltoluene (each isomer); aliphatic hydrocarbons such as cyclohexane, cyclopentane, cyclooctane and ethylcyclohexane; ketones such as methyl ethyl ketone and acetophenone; and dibutyl phthalate, dihexyl phthalate and dioctyl phthalate.

The reaction temperature of thermal decomposition reaction is preferably in the range of 100° C. to 350° C. High temperatures are preferred to increase the reaction rate. However, since the above-described side reaction may be caused by the N-substituted carbamic acid ester and/or the product isocyanate at high temperatures, the temperature is more preferably in the range of 150° C. to 250° C. Known cooling or heating apparatuses may be placed in the reactors to make the reaction temperature constant. Although the reaction pressure varies according to the type of the compound used and the reaction temperature, the reaction may be performed under reduced pressure, under normal pressure or under increased pressure and is preferably performed at a pressure in the range of 20 to $1 \times 10^6$ Pa. The reaction time (retention time in the case of the continuous method) is not particularly limited, and is preferably 0.001 to 100 hours, more preferably 0.005 to 50 hours, and still more preferably 0.01 to 10 hours.

It is preferred not to use a catalyst in thermal decomposition reaction. However, when a catalyst is used in any step in producing the N-substituted carbamic acid ester, the catalyst residue or the like may be supplied to the thermal decomposition step. Such a catalyst residue or the like may be present in this embodiment.

When the N-substituted carbamic acid ester is maintained at a high temperature for a long time, side reactions may be caused such as reaction of generating a urea bond-containing compound by a reaction to remove carbonic acid esters from two molecules of the N-substituted carbamic acid ester, and reaction of generating an allophanate group by reaction with the isocyanate group generated by thermal decomposition of the N-substituted carbamic acid ester, for example. Accordingly, the time during which the N-substituted carbamic acid ester and the isocyanate are maintained at a high temperature is preferably as short as possible. Therefore, the thermal decomposition reaction is preferably performed by the continuous method. The continuous method is a method in which a mixture containing the N-substituted carbamic acid ester is continuously supplied to a reactor and subjected to thermal decomposition reaction and the generated isocyanate and hydroxy compound are continuously extracted from the thermal decomposition reactor. In the continuous method, the low-boiling component generated by thermal decomposition reaction of the N-substituted carbamic acid ester is preferably recovered from the thermal decomposition reactor as a gas phase component, and the remainder is recovered from the bottom of the thermal decomposition reactor as a liquid phase component. Although all compounds present in the thermal decomposition reactor can be recovered as a gas phase component, a polymeric compound generated by side reaction caused by the N-substituted carbamic acid ester and/or isocyanate is dissolved and the polymeric compound is prevented from being attached to and accumulated on the thermal decomposition reactor by allowing a liquid phase component to be present in the thermal decomposition reactor. An isocyanate and a hydroxy compound are generated by thermal decomposition reaction of the N-substituted carbamic acid ester, and at least one of these compounds is recovered as a gas phase component. Which compound is recovered as a gas phase component depends on the thermal decomposition reaction conditions and the like.

Here, the term "low-boiling component generated by thermal decomposition reaction of the N-substituted carbamic acid ester" used in the present embodiment refers to a hydroxy compound and/or an isocyanate generated by thermal decomposition reaction of the N-substituted carbamic acid ester, in particular, a compound that may be present as a gas under the conditions where the thermal decomposition reaction is implemented.

It is possible to adopt a method of recovering the isocyanate and the hydroxy compound generated by thermal decomposition reaction as a gas phase component and recovering a liquid phase component containing the N-substituted carbamic acid ester, for example. In this method, the isocyanate and the hydroxy compound may be separately recovered by a thermal decomposition reactor.

When the liquid phase component contains the N-substituted carbamic acid ester, it is preferred to supply some or all of the liquid phase component to the upper part of the thermal decomposition reactor and subject the N-substituted carbamic acid ester to thermal decomposition reaction again. Here, the upper part of the thermal decomposition reactor refers to stages second or higher from the bottom of the column in terms of number of theoretical plates when the thermal decomposition reactor is a distillation column, and refers to a part above the heat transfer area being heated when the thermal decomposition reactor is a thin film distiller, for example. When some or all of the liquid phase component is supplied to the upper part of the thermal decomposition reactor, the liquid phase component is maintained preferably at 50° C. to 280° C., more preferably at 70° C. to 230° C., and still more preferably at 100° C. to 200° C. and transferred.

It is also possible to adopt a method of recovering the isocyanate and the hydroxy compound generated by thermal decomposition reaction as a gas phase component and recovering a liquid phase component containing the N-substituted carbamic acid ester from the bottom of the thermal decomposition reactor, for example. Also in this method, the gas component containing the recovered isocyanate is preferably supplied as a gas phase to a distillation apparatus for purifying and separating the isocyanate. On the other hand, it is preferred to supply some or all of the liquid phase component containing the N-substituted carbamic acid ester to the upper part of the thermal decomposition reactor and subject the N-substituted carbamic acid ester to thermal decomposition reaction again. When some or all of the liquid phase component is supplied to the upper part of the thermal decomposition reactor, the liquid phase component is maintained preferably at 50° C. to 180° C., more preferably at 70° C. to 170° C., and still more preferably at 100° C. to 150° C. and transferred.

It is further possible to adopt a method of recovering the hydroxy compound as a gas phase component from the isocyanate and the hydroxy compound generated by thermal decomposition reaction and recovering the mixture containing the isocyanate as a liquid phase component from the bottom of the thermal decomposition reactor, for example. In this case, the liquid phase component is supplied to the distillation apparatus and the isocyanate is recovered. When the liquid phase component contains the N-substituted carbamic acid ester, it is preferred to supply some or all of the mixture containing the N-substituted carbamic acid ester to the upper part of the thermal decomposition reactor and subject the N-substituted carbamic acid ester to thermal decomposition reaction again. When some or all of the liquid phase component is supplied to the upper part of the thermal decomposition reactor, the liquid phase component is maintained preferably at 50° C. to 180° C., more preferably at 70° C. to 170° C., and still more preferably at 100° C. to 150° C. and transferred.

As described above, in the thermal decomposition reaction, the liquid phase component is preferably recovered from the bottom of the thermal decomposition reactor. This is because a polymeric by-product generated by the above-described side reaction caused by the N-substituted carbamic acid ester and/or isocyanate can be dissolved and discharged from the thermal decomposition reactor as a liquid phase component by allowing the liquid phase component to be present in the thermal decomposition reactor. This reduces attachment to and accumulation on the thermal decomposition reactor of the polymeric compound.

When the liquid phase component contains the N-substituted carbamic acid ester, some or all of the liquid phase component is supplied to the upper part of the thermal decomposition reactor and the N-substituted carbamic acid ester is subjected to thermal decomposition reaction again, and when this step is repeated, a polymeric by-product may be accumulated in the liquid phase component. In this case, accumulation of the polymeric by-product can be reduced or the polymeric by-product can be maintained at a certain concentration by removing some or all of the liquid phase component from the reaction system.

Although the form of the thermal decomposition reactor is not particularly limited, a known distillation apparatus is preferably used to efficiently recover the gas phase component. For example, various known methods are used such as methods using reactors including any of distillation columns, multistage distillation columns, multitubular reactors, continuous multistage distillation columns, packed columns, thin film evaporators, reactors equipped with internal supports, forced circulation reactors, falling film evaporators and falling drop evaporators, as well as methods in which these methods are combined. In order to rapidly remove the low-boiling components from the reaction systems, methods using tubular reactors are preferred, and methods using reactors such as tubular thin film evaporators and tubular falling film evaporators are more preferred. Structures having a large gas-liquid contact area are preferred which can rapidly transfer the generated low-boiling component to the gas phase.

The materials for the thermal decomposition reactor and the line may be any known materials unless the N-substituted carbamic acid ester and the products such as the aromatic hydroxy compound and the isocyanate are adversely affected, and SUS304, SUS316, SUS316L and the like are inexpensive and can be preferably used.

<Separation Method According to the Present Embodiment>

The separation method according to the present embodiment comprises a step of separating at least either an active hydrogen-containing compound (A) or a compound (B) that reversibly reacts with (A) from a mixture containing (A) and (B) by distillation in a multistage distillation column; and a step of supplying the mixture to an inactive region formed within the multistage distillation column.

The term "inactive region" refers to a region inactive to the reaction between (A) and (B). Specifically, it refers to a region in which the effect of increasing the rate of reaction between (A) and (B) is small.

As described above, when distilling and separating a mixture of a plurality of compounds that can react with each other, these compounds often react with each other, so that the reaction product contaminates the distillation column, the recovery efficiency by distillation separation is reduced, or distillation separation itself cannot be performed. Surprisingly, the present inventors have found that the rate of reaction between (A) and (B) (for example, the reaction between (A) a hydroxy compound and/or a thiol and (B) an isocyanate and/or an isothiocyanate) is affected by the material and area of the part contacting with a mixture of (A) and (B), and this finding has led to the completion of the present invention.

A first aspect of the separation method of the present embodiment is a separation method where the multistage distillation column is a plate column, and the inactive region is a region in which the surface contacting with the mixture is formed of a material inactive to the reaction between (A) and (B).

A second aspect of the separation method of the present embodiment is a separation method where the multistage distillation column is a packed column, and the inactive region is a region in which the surface contacting with the mixture is packed with a packing material formed by a material inactive to the reaction between (A) and (B).

Surprisingly, the present inventors have found that the rate of reaction between (A) and (B) depends on the material of the part (region) contacting with a mixture of (A) and (B). As a result of extensive studies, the present inventors have found that materials containing specific amounts of various transition metal elements, in particular, materials containing specific amounts of transition metal elements of the third period, especially Fe, Ni or Ti elements are materials promoting the reaction between (A) and (B) (increasing the reaction rate).

Accordingly, the material used for the inactive region is preferably a material in which the Fe atom content, the Ni atom content and the Ti atom content are each 10 mass % or less. The Fe atom content, the Ni atom content and the Ti atom content are each more preferably 5 mass % or less, and still more preferably 2 mass % or less.

Components other than the Fe, Ni and Ti atoms in the packing material of the present embodiment are preferably silicon oxide (composition formula: $SiO_2$), aluminum oxide (composition formula: $Al_2O_3$) and carbon fluoride (a compound having a repeating unit —CHF— or $CF_2$—), for example. Glass, ceramics and fluororesins containing them as constituents are also preferred. In the case of glass and ceramics, the contents of silicon oxide and aluminum oxide are not particularly limited, and various materials can be selected, where the content of silicon oxide may be 60 mass % or more, or the content of aluminum oxide may be 60 mass % or more. Fluororesins include polytetrafluoroethylene, polychlorotrifluoroethylene, polyvinylidene fluoride, polyvinyl fluoride, a perfluoroalkoxyfluororesin, a tetrafluoroethylene-hexafluoropropylene copolymer, an ethylene-tetrafluoroethylene copolymer, and an ethylene-chlorotrifluoroethylene copolymer. Perferred packing materials illustrated here may contain other metal atoms without departing from the spirit of the present embodiment.

Although the preferred material or property thereof described above is preferably applied to the entire surface of the part contacting with a mixture containing (A) and (B) within a multistage distillation column, it may be difficult to apply it to the entire surface due to thermal resistance, mechanical strength and the like of the above-described material. Generally, when the multistage distillation column is a packed column, the surface of the structural material forming the packed column is often extremely small relative to the area of the surface of the packing material, and the influence of the surface of the structural material is extremely small. Accordingly, in the packed column, the preferred material described above can be applied to the packing material, and stainless steel or the like having high mechanical strength can be used for the structural material of the packed column, for example.

When a mixture containing (A) and (B) is supplied into a multistage distillation column and separated by distillation, the concentrations of (A) and (B) are generally changed continuously from the top to the bottom of the distillation column. Generally, in a packed column, the packing material made of the preferred material described above often has a height equivalent to a theoretical plate larger than that of a packing material made of stainless steel such as SUS316 or SUS304, for example, and it may not be preferred to pack all stages of a multistage packed column with the preferred packing material described above in terms of performance in separation of the mixture. Since the separation method of the present embodiment aims to suppress the reaction between (A) and (B) to efficiently recover (A) and/or (B) using a material inactive to the reaction between (A) and (B), it may not necessarily be appropriate to apply the preferred material described above to all stages. Accordingly, it is preferred to use the above-described inactive material for at least the stage within a multistage distillation column to which a mixture is supplied (one plate for a plate column or one theoretical plate for a packed column). It is more preferred to use the above-described material at a stoichiometric ratio of (A) to (B) ((A)/(B)) in a distillation column in the range of at least 0.2 to 5, preferably 0.01 to 100, and more preferably 0.001 to 1000. It is still more preferred to use the preferred material described above for all stages of a multistage packed column.

The pressure in performing distillation separation varies according to the composition of the components supplied to the multistage distillation column in which distillation separation is implemented, the temperature, the type of the multistage distillation column, and the like. For example, distillation separation is performed under reduced pressure, under atmospheric pressure and under increased pressure, but it is usually preferred to implement it at a pressure in the range of 0.01 kPa to 10 MPa, and the pressure is more preferably in the range of 0.1 kPa to 1 MPa, and still more preferably in the range of 0.5 kPa to 50 kPa in terms of easiness of industrial implementation.

The temperature in performing distillation separation varies according to the composition of the components supplied to the multistage distillation column in which distillation separation is implemented, the temperature, the type of the multistage distillation column, and the like. When the temperature is too high, (A), (B), and the later-described medium-boiling inactive compound, if used, may be thermally denatured and when the temperature is too low, industrial implementation is not easy, since a new installation for cooling must be provided, for example, and the temperature is therefore in the range of preferably 50° C. to 350° C., more preferably 80° C. to 300° C., and still more preferably 100° C. to 250° C.

In a multistage distillation column, installations attached to the multistage distillation column such as a line and a condenser are also preferably formed of the inactive material described above, but such a material is often inappropriate for constructing parts of the multistage packed column other than the packing material or structures such as a line in terms of strength or the like. In such a case, the inner walls of the parts of the multistage packed column other than the packing material, the line, and the like may be coated with the above-described material (by a method such as glass lining or Teflon® coating, for example). This also applies to the multistage distillation column itself and to the packing material when the multistage distillation column is a packed column.

The multistage distillation column may be any multistage distillation column that has three or more theoretical distillation plates and enables continuous distillation. On the other hand, when the number of theoretical plates is too large, the multistage distillation column is huge and its industrial implementation may be difficult. Accordingly, the number of stages (the number of plates for a plate column or the number of theoretical plates for a packed column) is preferably 500 or less. The shape of the packing material if used is not particularly limited, and various packing materials such as Raschig rings, Lessing rings, pall rings, Berl saddles, Intalox saddles, Dixon packings, McMahon packings, Heli Pack, Sulzer packings and Mellapak can be used.

A third aspect of the separation method of the present embodiment is a separation method where in the inactive region,
(X) the area of the inner surface of the multistage distillation column contacting with the mixture (unit: $m^2$) and
(Y) the volume of the mixture (unit: $m^3$)
satisfy $(X)/(Y) \leq 100$.

As described above, the reaction between (A) and (B) depends on the material of the part contacting with a mixture of (A) and (B), and the specific metal elements described above promote the reaction (increase the reaction rate). Additionally, the present inventors have found that the reaction rate also depends on the area of the part contacting with the mixture. Based on this finding, the present inventors present a distillation separation method by a multistage distillation column where (X) and (Y) satisfies $(X)/(Y) \leq 100$ in the inactive region formed within the multistage distillation column. By this method, the reaction between (A) and (B) is suppressed (the reaction is not promoted) and (A) and/or (B) can be efficiently separated by distillation.

The $(X)/(Y)$ value is preferably $(X)/(Y) \leq 100$, more preferably $(X)/(Y) \leq 70$, and still more preferably $(X)/(Y) \leq 50$.

The (X)/(Y) value in a multistage distillation column of the plate column method, for example, can be assessed to be acceptable if the (X)/(Y) value is defined on condition that the maximum amount of the liquid that can be retained in the stage where the (X)/(Y) value is to be evaluated is (Y), and that the inner surface area of the stage is defined as (X), and the value is within the preferred range described above. When the (X)/(Y) values in all stages of the multistage distillation column are evaluated, (X) and (Y) can be similarly defined for all stages. The (X)/(Y) value in a multistage distillation column of the packed column method, for example, can be assessed to be acceptable if the amount of the liquid retained in the column is measured in the state where the column is stably operated under the operation conditions similar to those during distillation, the (X)/(Y) value is defined on condition that the amount of the liquid retained in the column is defined as (Y) and the sum of the surface area of the packing material and the inner surface area of the packed column is defined as (X), and the value is within the preferred range described above.

When a mixture containing (A) and (B) is supplied into a multistage distillation column and separated by distillation, the concentrations of (A) and (B) are changed continuously from the top to the bottom of the distillation column and one of (A) and (B) is concentrated, generally. Because the method of the present embodiment aims to suppress the reaction between (A) and (B) to efficiently recover (A) and/or (B) by defining the area of the inner surface of the multistage distillation column contacting with the mixture of (A) and (B) within a specific range so that the reaction between (A) and (B) is not promoted, it is not necessarily required to apply the range to all stages. Accordingly, it is preferred to apply the above range to at least the stage within a multistage distillation column to which a mixture is supplied (one plate for a plate column or one theoretical plate for a packed column). It is more preferred to use a multistage distillation column satisfying the above range at a stoichiometric ratio of (A) to (B) ((A)/(B)) in the distillation column in the range of at least 0.2 to 5, preferably 0.01 to 100, and more preferably 0.001 to 1000. It is still more preferred to satisfy the preferred range described above for all stages of a multistage packed column.

The pressure in performing distillation separation varies according to the composition of the components supplied to the multistage distillation column in which distillation separation is implemented, the temperature, the type of the multistage distillation column, and the like. For example, distillation separation is performed under reduced pressure, under atmospheric pressure and under increased pressure, but it is usually preferred to implement it at a pressure in the range of 0.01 kPa to 10 MPa, and the pressure is more preferably in the range of 0.1 kPa to 1 MPa, and still more preferably in the range of 0.5 kPa to 50 kPa in terms of easiness of industrial implementation.

The temperature in performing distillation separation varies according to the composition of the components supplied to the multistage distillation column in which distillation separation is implemented, the temperature, the type of the multistage distillation column, and the like. When the temperature is too high, (A), (B), and the later-described medium-boiling inactive compound, if used, may be thermally denatured and when the temperature is too low, industrial implementation is not easy, since a new installation for cooling must be provided, for example, and the temperature is therefore in the range of preferably 50° C. to 350° C., more preferably 80° C. to 300° C., and still more preferably 100° C. to 250° C.

In a multistage distillation column, installations attached to the multistage distillation column such as a line and a condenser are also preferably formed of the inactive material described above, but such a material is often inappropriate for constructing parts of the multistage packed column other than the packing material or structures such as a line in terms of strength or the like. In such a case, the inner walls of the parts of the multistage packed column other than the packing material, the line, and the like may be coated with the above-described material (by a method such as glass lining or Teflon® coating, for example). This also applies to the multistage distillation column itself and to the packing material when the multistage distillation column is a packed column.

The multistage distillation column may be any multistage distillation column that has three or more theoretical distillation plates and enables continuous distillation. On the other hand, when the number of theoretical plates is too large, the multistage distillation column is huge and its industrial implementation may be difficult. Accordingly, the number of stages (the number of plates for a plate column or the number of theoretical plates for a packed column) is preferably 500 or less. The shape of the packing material if used is not particularly limited, and various packing materials such as Raschig rings, Lessing rings, pall rings, Berl saddles, Intalox saddles, Dixon packings, McMahon packings, Heli Pack, Sulzer packings and Mellapak can be used. However, when a multistage distillation column of the packed column method is used, the surface area within the multistage distillation column is often large, and in order to satisfy the preferred range of (X)/(Y) described above, the multistage distillation column often must be enlarged, and the amount of the mixture containing the (A) and the (B) supplied to the multistage distillation column often must be reduced (specifically, the throughput for distillation separation is often small relative to the size of the multistage distillation column). Therefore, a multistage distillation column of the plate column method is preferably used.

The compound to be separated by distillation by the separation method of the present embodiment is an active hydrogen-containing compound (A) or a compound (B) that reversibly reacts with (A). (A) is preferably a hydroxy compound and/or a thiol (including an aromatic thiol), more preferably a hydroxy compound, and still more preferably an aromatic hydroxy compound. (B) is preferably an isocyanate and/or an isothiocyanate, more preferably an isocyanate, and still more preferably an aliphatic isocyanate of the formula (20) where $R^4$ is an aliphatic group. The coupled product of (A) and (B) is not particularly limited, but given the scope of the present embodiment in which (A) and (B) are separated by distillation, the coupled product of (A) and (B) is a coupled product in which the difference in normal boiling point is preferably 5° C. or more, more preferably 10° C. or more, and still more preferably 15° C. or more.

<Separation Method in the Presence of Medium-Boiling Inactive Compound>

In the present embodiment, a method of performing distillation separation of (A) and (B) in the presence of a compound (C) that has a normal boiling point between the normal boiling point of (A) and the normal boiling point of (B) and is chemically inactive to (A) and (B) (herein also called "medium-boiling inactive compound") is also preferably implemented.

The "medium-boiling inactive compound" refers to a compound that has a normal boiling point between the normal boiling point of (A) and the normal boiling point of (B) and is chemically inactive to both (A) and (B).

Specifically, the medium-boiling inactive compound is first characterized by being "chemically inactive" to (A) and (B). The term "chemically inactive" means not having reactivity to (A) and (B). The medium-boiling inactive compound is a compound not forming a covalent bond with each of (A) and (B) or separate from (A) and (B) at the distillation operation temperature.

The medium-boiling inactive compound is preferably a compound not having a functional group reactive with (A) and (B), and more preferably a compound not having active hydrogen.

Examples of the medium-boiling inactive compound include at least one compound selected from the group consisting of (1) a hydrocarbon compound having a linear, branched or cyclic structure, (2) a compound in which the same or different hydrocarbon compounds having a linear, branched or cyclic structure are bonded to each other via an ether bond or a thioether bond (specifically, a compound in which two hydrocarbon compounds are bonded to each other via an ether bond or a thioether bond; the hydrocarbon compound has a linear, branched or cyclic structure, and the two hydrocarbon compounds may be the same or different), (3) an aromatic hydrocarbon compound which may have a substituent composed of a hydrocarbon group, (4) a compound in which the same or different aromatic hydrocarbon compounds are bonded to each other via an ether bond or a thioether bond, (5) a compound in which a hydrocarbon compound having a linear, branched or cyclic structure and an aromatic hydrocarbon compound are bonded to each other via an ether bond or a thioether bond, and (6) a halogenated compound in which at least one hydrogen atom forming a hydrocarbon compound having a linear, branched or cyclic structure or at least one hydrogen atom forming an aromatic hydrocarbon compound which may have a substituent composed of a hydrocarbon group is replaced with a halogen atom.

Specific examples of the medium-boiling inactive compound include hydrocarbon compounds such as pentane (each isomer), hexane (each isomer), heptane (each isomer), octane (each isomer), nonane (each isomer), decane (each isomer), dodecane (each isomer), tetradecane (each isomer), pentadecane (each isomer), hexadecane (each isomer), octadecane (each isomer) and nonadecane (each isomer); ethers in which hydrocarbon compounds are bonded to each other via an ether bond, such as octyl ether (each isomer), nonyl ether (each isomer), decyl ether (each isomer), dodecyl ether (each isomer), tetradecyl ether (each isomer), pentadecyl ether (each isomer), hexadecyl ether (each isomer), octadecyl ether (each isomer), nonadecyl ether (each isomer) and tetraethylene glycol dimethyl ether; thioethers in which hydrocarbon compounds are bonded to each other via a thioether bond, such as dimethyl sulfide, diethyl sulfide, dibutyl sulfide (each isomer), dihexyl sulfide (each isomer), octyl sulfide (each isomer), nonyl sulfide (each isomer), decyl sulfide (each isomer), dodecyl sulfide (each isomer), tetradecyl sulfide (each isomer), pentadecyl sulfide (each isomer), hexadecyl sulfide (each isomer), octadecyl sulfide (each isomer) and nonadecyl sulfide (each isomer); aromatic hydrocarbon compounds such as benzene, toluene, ethylbenzene, butylbenzene (each isomer), pentylbenzene (each isomer), hexylbenzene (each isomer), octylbenzene (each isomer), biphenyl, terphenyl, diphenylethane (each isomer), (methylphenyl)phenylethane (each isomer), dimethylbiphenyl (each isomer) and benzyltoluene (each isomer); aromatic ethers in which aromatic hydrocarbon compounds are bonded to each other via an ether bond, such as diphenyl ether, di(methylbenzyl)ether (each isomer), di(ethylbenzyl) ether (each isomer), di(butylbenzyl)ether (each isomer), di(pentylbenzyl)ether (each isomer), di(hexylbenzyl)ether (each isomer), di(octylbenzyl)ether (each isomer), diphenyl ether and dibenzyl ether; aromatic thioethers in which aromatic hydrocarbon compounds are bonded to each other via a thioether bond, such as diphenyl sulfide, di(methylbenzyl) sulfide (each isomer), di(ethylbenzyl) sulfide (each isomer), di(butylbenzyl) sulfide (each isomer), di(pentylbenzyl) sulfide (each isomer), di(hexylbenzyl) sulfide (each isomer), di(octylbenzyl) sulfide (each isomer), di(methylphenyl) sulfide and dibenzyl sulfide; compounds in which a hydrocarbon compound and an aromatic hydrocarbon compound are bonded to each other via an ether bond, such as methoxybenzene, ethoxybenzene, butoxybenzene (each isomer), dimethoxybenzene (each isomer), diethoxybenzene (each isomer) and dibutoxybenzene (each isomer); and halogenated compounds such as chloromethane, chloroethane, chloropentane (each isomer), chlorooctane (each isomer), bromomethane, bromoethane, bromopentane (each isomer), bromooctane (each isomer), dichloroethane (each isomer), dichloropentane (each isomer), dichlorooctane (each isomer), dibromoethane (each isomer), dibromopentane (each isomer), dibromooctane (each isomer), chlorobenzene, bromobenzene, dichlorobenzene, dibromobenzene, benzyl chloride and benzyl bromide.

Compounds having an ether bond or a thioether bond such as the above (2), (4) and (5) may generate oxides and peroxides depending on the conditions. Accordingly, (1) a hydrocarbon compound having a linear, branched or cyclic structure, (3) an aromatic hydrocarbon compound which may have a substituent composed of a hydrocarbon group, and (6) a halogenated compound in which at least one hydrogen atom forming a hydrocarbon compound having a linear, branched or cyclic structure or at least one hydrogen atom forming an aromatic hydrocarbon compound which may have a substituent composed of a hydrocarbon group is replaced with a halogen atom are preferred in terms of thermal stability. Compounds containing a halogen atom such as (6) may be decomposed or generate a halogen radical, and the halogenated compounds may be mixed in the products, depending on the conditions. Accordingly, (1) a hydrocarbon compound having a linear, branched or cyclic structure and (3) an aromatic hydrocarbon compound which may have a substituent composed of a hydrocarbon group are more preferred.

The medium-boiling inactive compound is also characterized in that the normal boiling point of the medium-boiling inactive compound is a temperature between the normal boiling point of (A) and the normal boiling point of (B). Specifically, the normal boiling point of the medium-boiling inactive compound (Tc° C.) relative to the normal boiling point of (A) to be separated (Ta° C.) and the normal boiling point of (B) to be separated (Tb° C.) is Tb<Tc<Ta or Ta<Tc<Tb. The medium-boiling inactive compound can be appropriately selected and used together with (A) and (B). Here, the normal boiling point represents a boiling point at 1 atm. It is difficult to define a normal boiling point by a structure such as a general formula, and the normal boiling point is measured or investigated and selected for each compound. The normal boiling point can be measured by a known method such as the method defined in the Japanese Pharmacopoeia, Fourteenth Edition, Part I, 54, for example, and persons skilled in the art can usually implement such a method.

The normal boiling point of the medium-boiling inactive compound (Tc° C.) differs from the normal boiling point of (B) to be separated (Tb° C.) and the normal boiling point of (A) to be separated (Ta° C.) by preferably 5° C. or more, and more preferably 10° C. or more. In this case, it is easy to separate (A) and the medium-boiling inactive compound or separate the medium-boiling inactive compound and (B). The fact that the normal boiling point of the medium-boiling inactive compound differs from the normal boiling point of (A) and the normal boiling point of (B) by 5° C. or more does not form the basis of the present embodiment. However, it is assumed that the normal boiling points of the two components to be separated preferably differ from each other by 5° C. or more due to easiness of the steps that may occur after separation of (A) and (B), based on the finding that they can be industrially sufficiently separated by distillation when the normal boiling points differ from each other by 5° C. or more.

Preferably, a mixture containing (A) and (B) is supplied to a layer formed of the medium-boiling inactive compound described above in a multistage distillation column, and (A) and (B) are separated and recovered in the multistage distillation column. Specifically, when the mixture containing (A) and (B) is supplied to the multistage distillation column, the ratio of the area of the part contacting with the mixture to the volume of the mixture is preferably within the above-described range, and additionally, a layer formed of the medium-boiling inactive compound is preferably formed in the multistage distillation column at a height where a supply port is provided to which the mixture of (A) and (B) is supplied.

A mixture containing (A) and (B) is supplied to the middle of a multistage packed column. Here, the "middle" is a position in the multistage distillation column which is between the top and the bottom of the column in the height direction and where at least one stage (one theoretical plate for a packed column), preferably at least three stages (three theoretical plates for a packed column), may be present over and under the stage provided with a supply port, respectively. The top of the column refers to the uppermost part of the multistage distillation column from which a gas phase is continuously extracted, and the bottom of the column refers to the lowermost part of the multistage distillation column.

The "layer formed of the medium-boiling inactive compound" in the present embodiment refers to a layer mainly formed by the medium-boiling inactive compound described above. The separation method of the present embodiment is a separation method of supplying a mixture containing (A) and (B) to an inactive region formed within a multistage distillation column, and separating (A) and (B) by distillation in the multistage distillation column, where the multistage distillation column is a plate column, and the surface of the inactive region contacting with the mixture is formed of a material inactive to the reaction between (A) and (B), or where the multistage distillation column is a packed column, and the inactive region is a region in which the surface contacting with the mixture is formed of a packing material formed by a material inactive to the reaction between (A) and (B). By supplying the mixture of (A) and (B) to the layer formed of the medium-boiling inactive compound and separating and/or diluting (A) and (B) in addition to such a separation method, the reaction between (A) and (B) by contact between (A) and (B) can be suppressed, and (A) and (B) can be more efficiently separated.

The layer formed of the medium-boiling inactive compound in the present embodiment is formed in the range of at least one stage, preferably at least three stages, over and under a supply port, respectively. The content of the medium-boiling inactive compound in the liquid phase and/or the gas phase, preferably the liquid phase and the gas phase, of the layer formed of the medium-boiling inactive compound is preferably 5 mass % or more, more preferably 10 mass % or more, and still more preferably 30 mass % or more. The content of the medium-boiling inactive compound can be determined by sampling the liquid phase component and/or the gas phase component from the multistage distillation column and analyzing by a known method such as gas chromatography or liquid chromatography. The content of the medium-boiling inactive compound may also be estimated from the temperature and pressure in a random position in the multistage packed column using a previously determined T-XY diagram of components in the multistage distillation column.

The range of the layer formed of the medium-boiling inactive compound can be adjusted by controlling the amount of heat given to the evaporator provided at the bottom of the multistage distillation column, the amount of reflux at the top of the multistage distillation column, the amount of the medium-boiling inactive compound supplied, the amount of the mixture containing (A) and (B) supplied, the pressure within the multistage packed column, and the like. Optionally, the medium-boiling inactive compound may be present in stages other than in the above-described range.

On the other hand, when the mixture starts to be supplied to the multistage distillation column, it is preferred to use a method of introducing only the medium-boiling inactive compound into the multistage distillation column, boiling the medium-boiling inactive compound so that the gas phase portion is filled with a gas of the medium-boiling inactive compound, and then supplying the mixture to the multistage distillation column in this state, and it is more preferred to supply the mixture to the multistage distillation column under total reflux of the medium-boiling inactive compound.

The medium-boiling inactive compound can be supplied to the multistage distillation column either as a liquid or as a gas. The medium-boiling inactive compound may be supplied from any position in the multistage distillation column, specifically, may be supplied from a supply port provided in the upper part of the multistage distillation column, may be supplied from a supply port provided in the lower part of the multistage distillation column, may be supplied from a supply port provided at a height the same as that of a supply port to which the mixture is supplied, or may be supplied from a supply port to which the mixture is supplied.

The amount of the medium-boiling inactive compound used is preferably 0.01 to 100 times based on the mass of the mixture, depending on the compounds used, the compounds to be separated, and the operation conditions. The amount of the medium-boiling inactive compound used is preferably an excess in order to suppress the reaction between (A) and (B), but too large an excess is not preferred because the throughput in the packed column (the amount of the mixture containing (A) and (B) supplied) is reduced. Accordingly, the amount of the medium-boiling inactive compound used is more preferably 0.1 to 50 times, and still more preferably 0.3 to 30 times, based on the mass of the mixture.

The pressure in performing distillation separation varies according to the composition of the components supplied to the multistage distillation column in which distillation separation is implemented, the temperature, the type of the multistage distillation column, and the like. For example, distillation separation is performed under reduced pressure, under atmospheric pressure and under increased pressure, but it is usually preferred to perform it at a pressure in the range of 0.01 kPa to 10 MPa, and the pressure is more preferably in the range of 0.1 kPa to 1 MPa, and still more preferably in the range of 0.5 kPa to 50 kPa in terms of easiness of industrial implementation.

The temperature in performing distillation separation varies according to the composition of the components supplied to the multistage packed column in which distillation separation is implemented, the temperature, the type of the multistage packed column, and the like. When the temperature is too high, (A), (B), and the medium-boiling inactive compound may be thermally denatured and when the temperature is too low, industrial implementation is not easy, since a new installation for cooling must be provided, for example, and the temperature is therefore in the range of preferably 50° C. to 350° C., more preferably 80° C. to 300° C., and still more preferably 100° C. to 250° C.

EXAMPLES

The present invention will be specifically described below with reference to examples; however, the scope of the present invention is not limited to these examples.

<Analysis Method>
(1) NMR Analysis Method
Apparatus: JNM-A400 FT-NMR system manufactured by JEOL Ltd.
(1-1) Preparation of $^1$H-NMR Analysis Sample and $^{13}$C-NMR Analysis Sample
About 0.3 g of a sample solution was weighed, about 0.7 g of deuterated chloroform (manufactured by Aldrich, 99.8%) and 0.05 g of tetramethyltin as the internal standard (manufactured by Wako Pure Chemical Industries, Ltd., Wako 1st Grade) were added, and they are homogeneously mixed to prepare a solution as an NMR analysis sample.
(1-2) Quantitative Analysis Method
Each standard was analyzed to prepare a calibration curve, and the analysis sample solution was quantitatively analyzed based on the calibration curve.
(2) Liquid Chromatography Analysis Method
Apparatus: LC-10AT system manufactured by Shimadzu Corp.
Column: Silica-60 column manufactured by Tosoh Corp., two columns connected in series
Developing solvent: Mixture of hexane/tetrahydrofuran=80/20 (volume ratio)
Solvent flow rate: 2 mL/min
Column temperature: 35° C.
Detector: R.I. (refractometer)
(2-1) Liquid Chromatography Analysis Sample
About 0.1 g of a sample was weighed, about 1 g of tetrahydrofuran (manufactured by Wako Pure Chemical Industries, Ltd., dehydrated) and about 0.02 g of bisphenol A as the internal standard (manufactured by Wako Pure Chemical Industries, Ltd., 1st Grade) were added, and they are homogeneously mixed to prepare a solution as a liquid chromatography analysis sample.
(2-2) Quantitative Analysis Method
Each standard was analyzed to prepare a calibration curve, and the analysis sample solution was quantitatively analyzed based on the calibration curve.
(3) Gel Permeation Chromatography (GPC) Analysis Method
Apparatus: LC-10AT system manufactured by Shimadzu Corp.
Column: TSKgel G1000H$_{XL}$ manufactured by Tosoh Corp., three columns connected in series
Developing solvent: Chloroform
Solvent flow rate: 2 mL/min
Column temperature: 35° C.
Detector: R.I. (refractometer)
(3-1) Gel Permeation Chromatography Analysis Sample
About 0.1 g of a sample was weighed, about 1 g of chloroform was added, and they are homogeneously mixed to prepare a solution as an analysis sample.
(3-2) Quantitative Analysis Method
A calibration curve relative to the retention time was prepared using monodisperse polystyrene as the standard sample, and the molecular weight was calculated from the calibration curve.

Example 1

<Step (1-1)>
12.1 kg (72 mol) of hexamethylene diisocyanate was mixed with 0.98 g (3.6 mol) of propoxylated glycerol having one propylene oxide group on average per hydroxy group. 0.5 g of zinc acetate was added to this solution, and the mixture was heated at 120° C. for about 1.5 hours. The reaction solution was analyzed by GPC to find that the number average molecular weight for the parts excluding the peaks corresponding to the isocyanate and propoxylated glycerol raw materials was 5.9×10$^2$. 0.5 ml of diethylhexyl phosphate was added to the mixture.
<Step (1-2)>
The unreacted monomers were separated by distillation using a distillation separation unit 100 shown in FIG. 1.
The reaction solution obtained in Step (1-1) was supplied from a line 10 to a continuous multistage packed column 101 packed with a Raschig ring made of ceramic (Ti atom content: 0.809 mass %, Fe atom content: 0.699 mass %, Ni atom content: 0.01 mass %). Distillation separation was performed with the temperature of the continuous multistage packed column 101 at 120° C. and the internal pressure at 0.2 kPa. The part below the part connected with the line 10 in the continuous multistage packed column 101 was heated with a heat medium jacket. The hexamethylene diisocyanate was recovered from a line 11, the propoxylated glycerol was recovered from a line 17, and the polyisocyanate was recovered from a line 16. The resulting polyisocyanate was measured by GPC to find that the number average molecular weight was 6.0×10$^2$.

Reference Example 1

Figure 2:
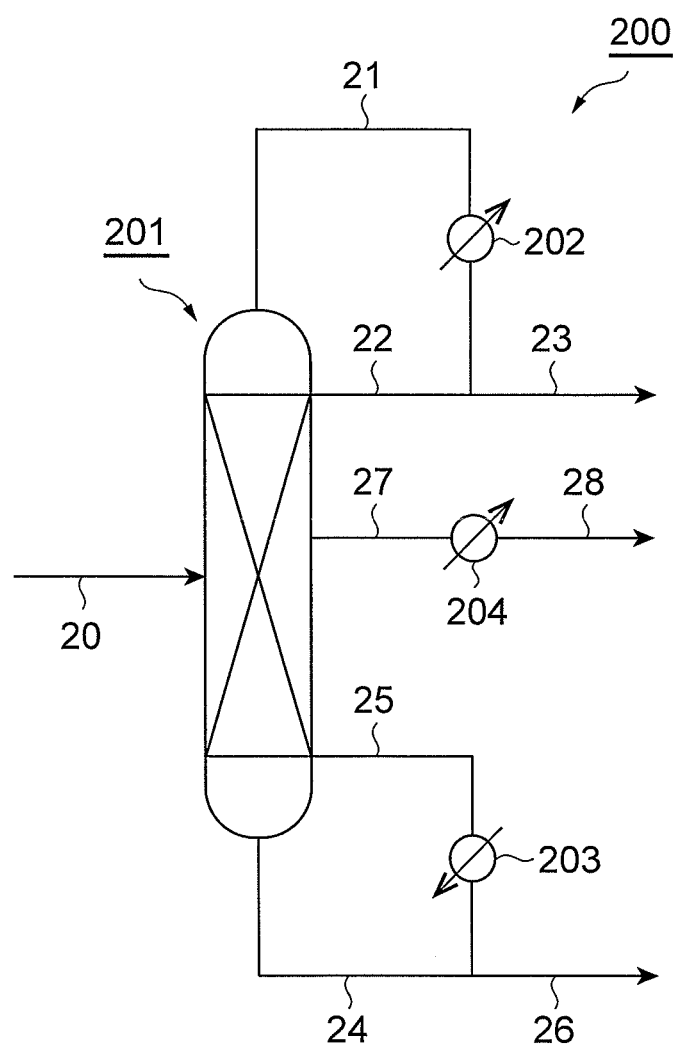
FIG. 2 is an illustration showing a distillation separation unit according to an embodiment.

<Step (A-1)>
The reaction similar to that in Step (1-1) of Example 1 was performed. The reaction solution was analyzed by GPC to find that the number average molecular weight for the parts excluding the peaks corresponding to the isocyanate and propoxylated glycerol raw materials was 5.9×10$^2$. 0.5 ml of diethylhexyl phosphate was added to the mixture.
<Step (A-2)>
A distillation separation unit 200 shown in FIG. 2 was used.
The reaction solution obtained in Step (A-1) was supplied from a line 20 to a continuous multistage packed column 201 packed with a Raschig ring made of SUS316 (Fe atom content: 67 mass % or more, Ni atom content: 12 mass %). Distillation separation was performed with the temperature of the continuous multistage packed column 201 at 120° C. and the internal pressure at 0.2 kPa. The part below the part connected with the line 20 in the continuous multistage packed column 201 was heated with a heat medium jacket. The hexamethylene diisocyanate was recovered from a line 21, the propoxylated glycerol was recovered from a line 27, and the polyisocyanate was recovered from a line 26. The resulting polyisocyanate was measured by GPC to find that the number average molecular weight was $9.1 \times 10^2$.

Presumably, in Step (A-2), Fe on the surface of the Raschig ring made of SUS316 promoted polyisocyanate formation reaction in the continuous multistage packed column 201, and changed the number average molecular weight of the polyisocyanate after performing Step (A-2).

Example 2

<Step (2-1)>

The reaction similar to that in Step (1-1) of Example 1 was performed. The reaction solution was analyzed by GPC to find that the number average molecular weight for the parts excluding the peaks corresponding to the isocyanate and propoxylated glycerol raw materials was $5.9 \times 10^2$. 0.5 ml of diethylhexyl phosphate was added to the mixture.

<Step (2-2)>

Figure 3:
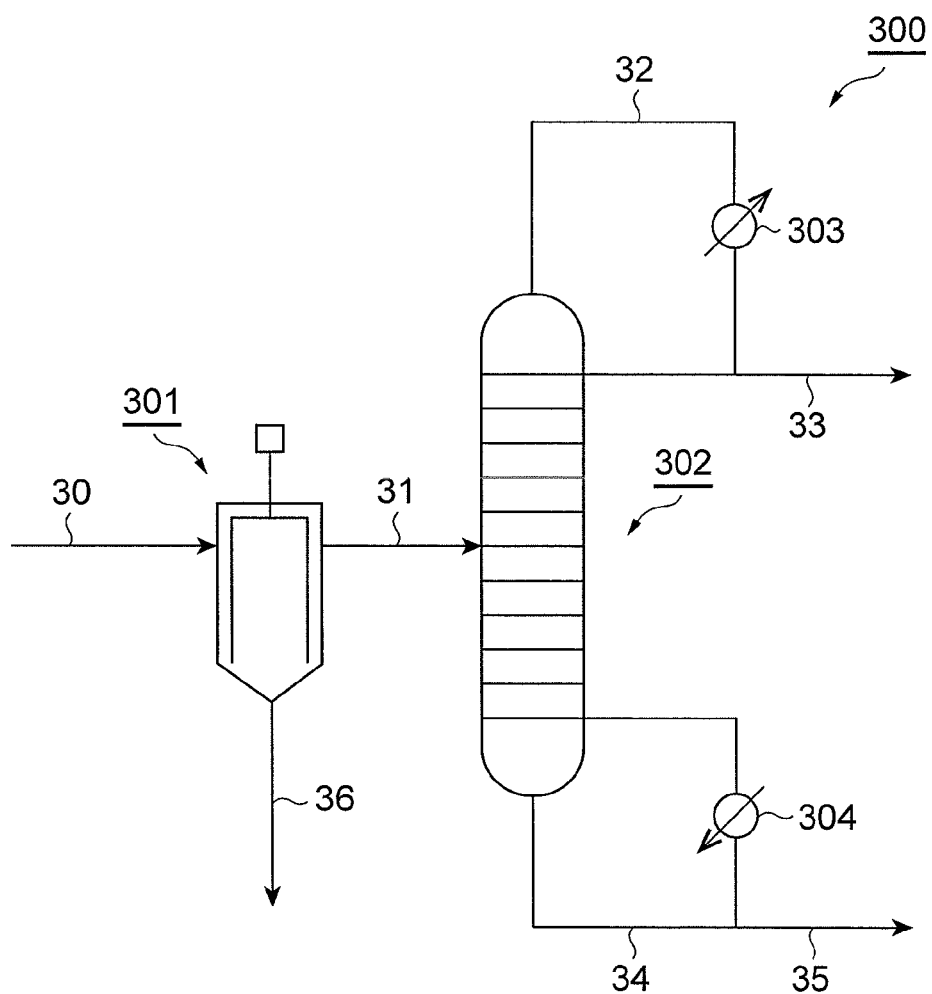
FIG. 3 is an illustration showing a distillation separation unit according to an embodiment.

The unreacted monomers were separated by distillation using a distillation separation unit 300 shown in FIG. 3.

The reaction solution obtained in Step (2-1) was heated to 150° C. and supplied to a thin film distillation apparatus 301 having an internal pressure of 0.4 kPa. The polyisocyanate recovered from a line 36 was measured by GPC to find that the number average molecular weight was $6.1 \times 10^2$. Meanwhile, the unreacted monomers were extracted as gas components from a line 31 and supplied to a continuous multistage distillation column 302 (Oldershaw column made of glass, stages). The liquid recovered from a line 33 was the hexamethylene diisocyanate. The liquid recovered from a line 35 was the propoxylated glycerol.

Reference Example 2

<Step (B-1)>

The reaction similar to that in Step (1-1) of Example 1 was performed. The reaction solution was analyzed by GPC to find that the number average molecular weight for the parts excluding the peaks corresponding to the isocyanate and propoxylated glycerol raw materials was $5.9 \times 10^2$. 0.5 ml of diethylhexyl phosphate was added to the mixture.

<Step (B-2)>

Figure 4:
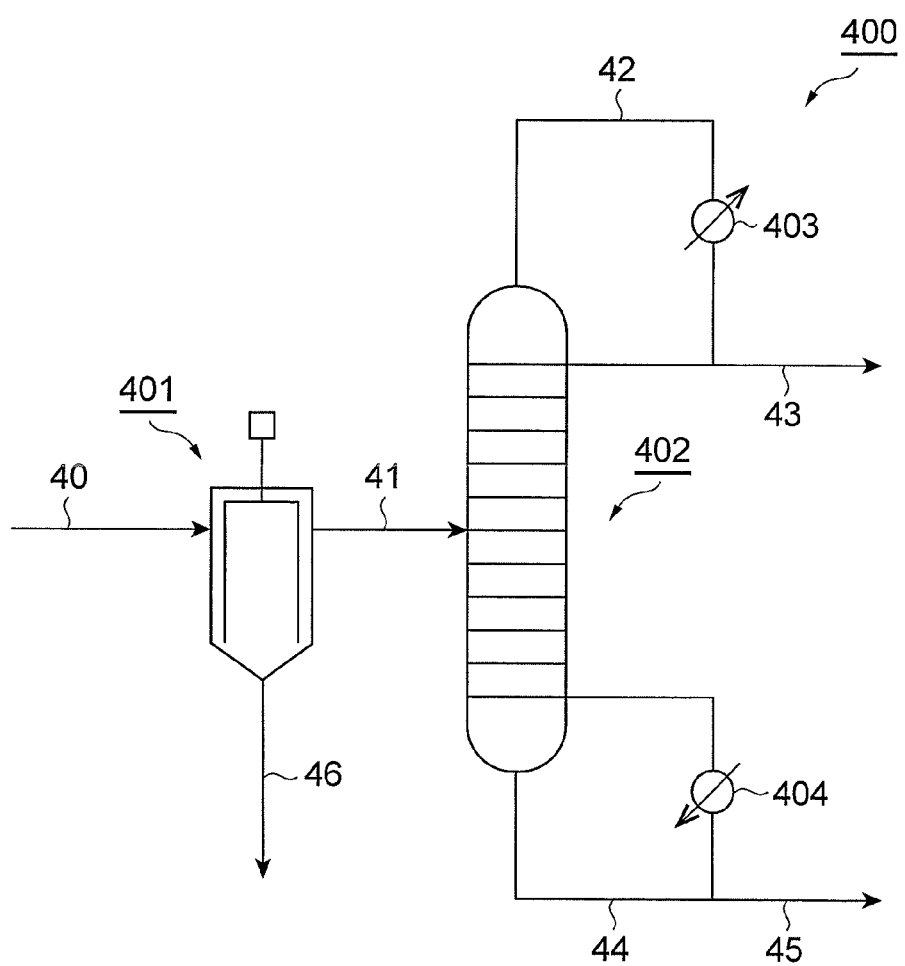
FIG. 4 is an illustration showing a distillation separation unit according to an embodiment.

The unreacted monomers were separated by distillation using a distillation separation unit 400 shown in FIG. 4.

The reaction solution obtained in Step (B-1) was heated to 150° C. and supplied to a thin film distillation apparatus 401 having an internal pressure of 0.4 kPa. The polyisocyanate recovered from a line 46 was measured by GPC to find that the number average molecular weight was $6.1 \times 10^2$. The unreacted monomers were extracted as gas components from a line 41 and supplied to a continuous multistage distillation column 402 (Oldershaw column made of SUS316, having the same size and number of stages as those of the continuous multistage distillation column 302 used in Step (2-2) of Example 2). The liquid recovered from a line 43 was the hexamethylene diisocyanate. On the other hand, the liquid recovered from a line 45 was a compound in which some of the hydroxy groups of the propoxylated glycerol reacted with isocyanate groups, and its number average molecular weight by GPC measurement was $3.8 \times 10^2$.

Presumably, in Step (B-2), Fe on the surface of the Oldershaw column made of SUS316 promoted reaction of the hexamethylene diisocyanate with the propoxylated glycerol, and generated a compound in which some of the hydroxy groups of the propoxylated glycerol reacted with isocyanate groups.

Example 3

<Step (3-1)>

12.0 kg (54 mol) of isophorone diisocyanate was mixed with 1.98 g (7.2 mol) of propoxylated glycerol having one propylene oxide group on average per hydroxy group. 0.5 g of zinc acetate was added to this solution, and the mixture was heated at 120° C. for about 0.5 hour. The reaction solution was analyzed by GPC to find that the number average molecular weight for the parts excluding the peaks corresponding to the isocyanate and propoxylated glycerol raw materials was $8.1 \times 10^2$. 0.5 ml of diethylhexyl phosphate was added to the mixture.

<Step (3-2)>

The unreacted monomers were separated by distillation using a distillation separation unit 300 shown in FIG. 3.

The reaction solution obtained in Step (3-1) was heated to 150° C. and supplied to a thin film distillation apparatus 301 having an internal pressure of 0.1 kPa. The polyisocyanate recovered from a line 36 was measured by GPC to find that the number average molecular weight was $8.2 \times 10^2$. Meanwhile, the unreacted monomers were extracted as gas components from a line 31 and supplied to a continuous multistage distillation column 302 (Oldershaw column made of glass, 15 stages). The liquid recovered from a line 33 contained the isophorone diisocyanate at 98 mass %. The liquid recovered from a line 35 contained the propoxylated glycerol at 98 mass %.

Reference Example 3

<Step (C-1)>

The reaction similar to that in Step (3-1) of Example 3 was performed. The reaction solution was analyzed by GPC to find that the number average molecular weight for the parts excluding the peaks corresponding to the isocyanate and propoxylated glycerol raw materials was $8.1 \times 10^2$. 0.5 ml of diethylhexyl phosphate was added to the mixture.

<Step (C-2)>

The unreacted monomers were separated by distillation using a distillation separation unit 400 shown in FIG. 4.

The reaction solution obtained in Step (C-1) was heated to 150° C. and supplied to a thin film distillation apparatus 401 having an internal pressure of 0.4 kPa. The polyisocyanate recovered from a line 46 was measured by GPC to find that the number average molecular weight was $8.1 \times 10^2$. The unreacted monomers were extracted as gas components from a line 41 and supplied to a continuous multistage distillation column 402 (Oldershaw column made of SUS316, having the same size as that of the continuous multistage distillation column 302 used in Step (3-2) of Example 3). The liquid recovered from a line 43 was the hexamethylene diisocyanate. On the other hand, the liquid recovered from a line 45 was a mixture of the propoxylated glycerol with a compound in which some of the hydroxy groups of the propoxylated glycerol reacted with isocyanate groups, and its number average molecular weight by GPC measurement was $4.8 \times 10^2$.

Example 4

<Step (4-1)>

97.0 kg (500 mol) of butylphenyl carbonate was heated to 120° C. in a nitrogen atmosphere. 11.6 kg (100 mol) of hexamethylenediamine was then added and stirring was continued for five hours. The reaction solution was analyzed by liquid chromatography and $^1$H-NMR to find that it was a mixture containing N,N'-hexanediyl-dicarbamic acid dibutyl ester, butylphenyl carbonate and phenol.

<Step (4-2)>

Figure 5:
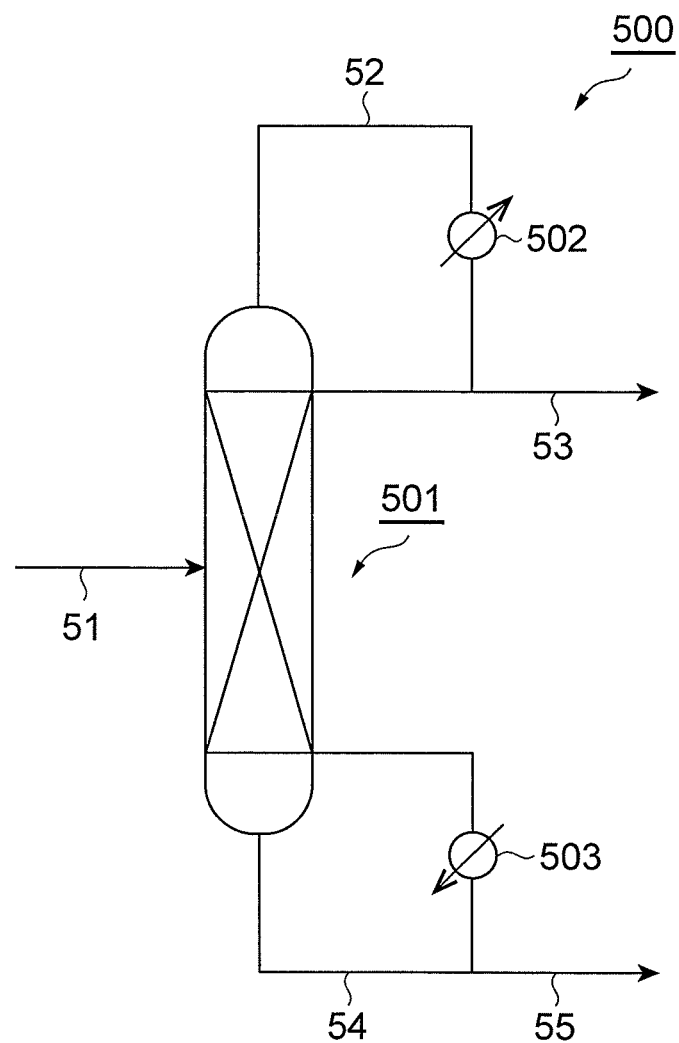
FIG. 5 is an illustration showing a distillation separation unit according to an embodiment.

Distillation separation was performed in a distillation separation unit 500 shown in FIG. 5.

The reaction solution obtained in Step (4-1) was supplied from a line 51 to a continuous multistage packed column 501 packed with a Raschig ring made of ceramic (manufactured by Matsui Machine Ltd.). Distillation separation was performed with the temperature of the continuous multistage packed column 501 at 90° C. and the internal pressure at 0.2 kPa. The phenol was recovered from a line 53, and the N,N'-hexanediyl-dicarbamic acid dibutyl ester and butylphenyl carbonate were recovered from a line 55. Dibutyl carbonate was not detected in the mixture recovered from the line 55.

Reference Example 4

<Step (D-1)>

A mixture containing N,N'-hexanediyl-dicarbamic acid dibutyl ester, butylphenyl carbonate and phenol was obtained by performing reaction similar to that in Step (4-1) of Example 4.

<Step (D-2)>

Figure 6:
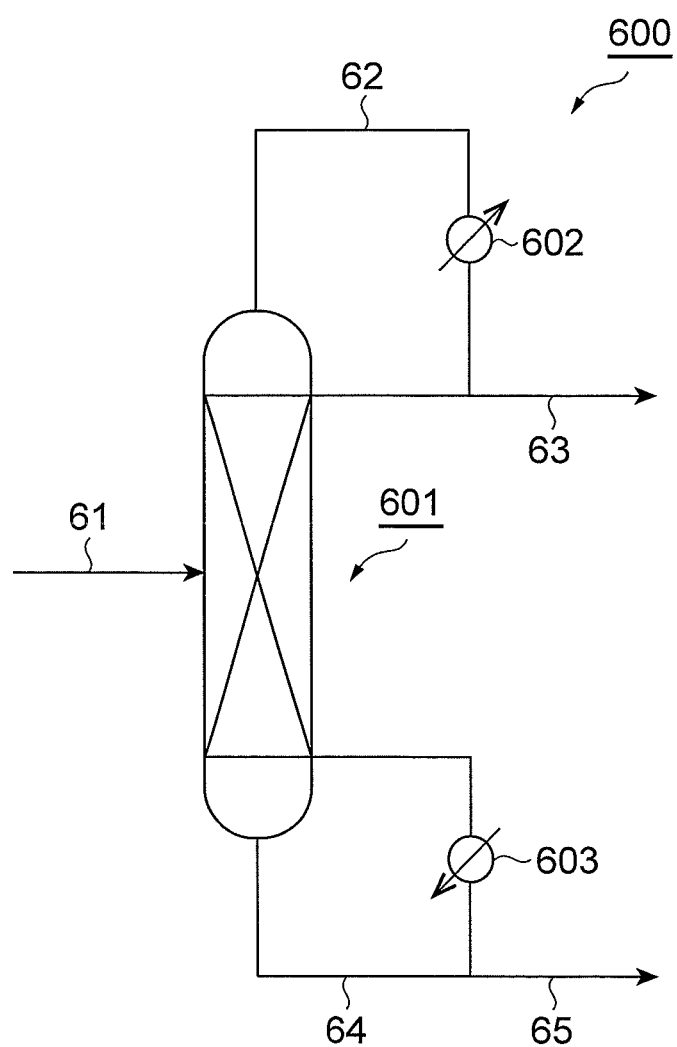
FIG. 6 is an illustration showing a distillation separation unit according to an embodiment.

The phenol was separated by distillation in a distillation separation unit 600 shown in FIG. 6.

The reaction solution obtained in Step (D-1) was supplied from a line 61 to a continuous multistage packed column 601 packed with a Raschig ring made of SUS304. Distillation separation was performed with the temperature of the continuous multistage packed column 601 at 90° C. and the internal pressure at 0.2 kPa. The phenol and butanol were recovered from a line 63. A mixture containing the N,N'-hexanediyl-dicarbamic acid dibutyl ester, a compound represented by the following formula (a), the butylphenyl carbonate and diphenyl carbonate was recovered from a line 65.

[Chemical Formula 32]

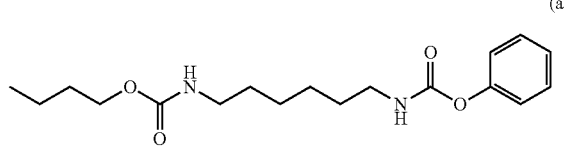

(a)

Presumably, in the continuous multistage packed column 601, the Fe-containing surface of the Raschig ring made of SUS304 promoted ester exchange reaction between butylphenyl carbonate and phenol, so that its product, diphenyl carbonate, was recovered from the bottom of the continuous multistage packed column 601 and the other product, butanol was recovered from the top of the continuous multistage packed column 601, while the surface promoted ester exchange reaction between N,N'-hexanediyl-dicarbamic acid dibutyl ester and phenol, so that its product, the compound represented by the formula (a), was recovered from the bottom of the continuous multistage packed column 601.

Example 5

<Step (5-1)>

67.9 kg (350 mol) of butylphenyl carbonate was heated to 120° C. in a nitrogen atmosphere. 10.5 kg (50 mol) of 4,4'-dicyclohexylmethanediamine was then added and stirring was continued for five hours. The reaction solution was analyzed by liquid chromatography and $^1$H-NMR to find that it was a mixture containing 4,4'-dicyclohexylmethanedi (carbamic acid butyl ester), butylphenyl carbonate and phenol.

<Step (5-2)>

Figure 7:
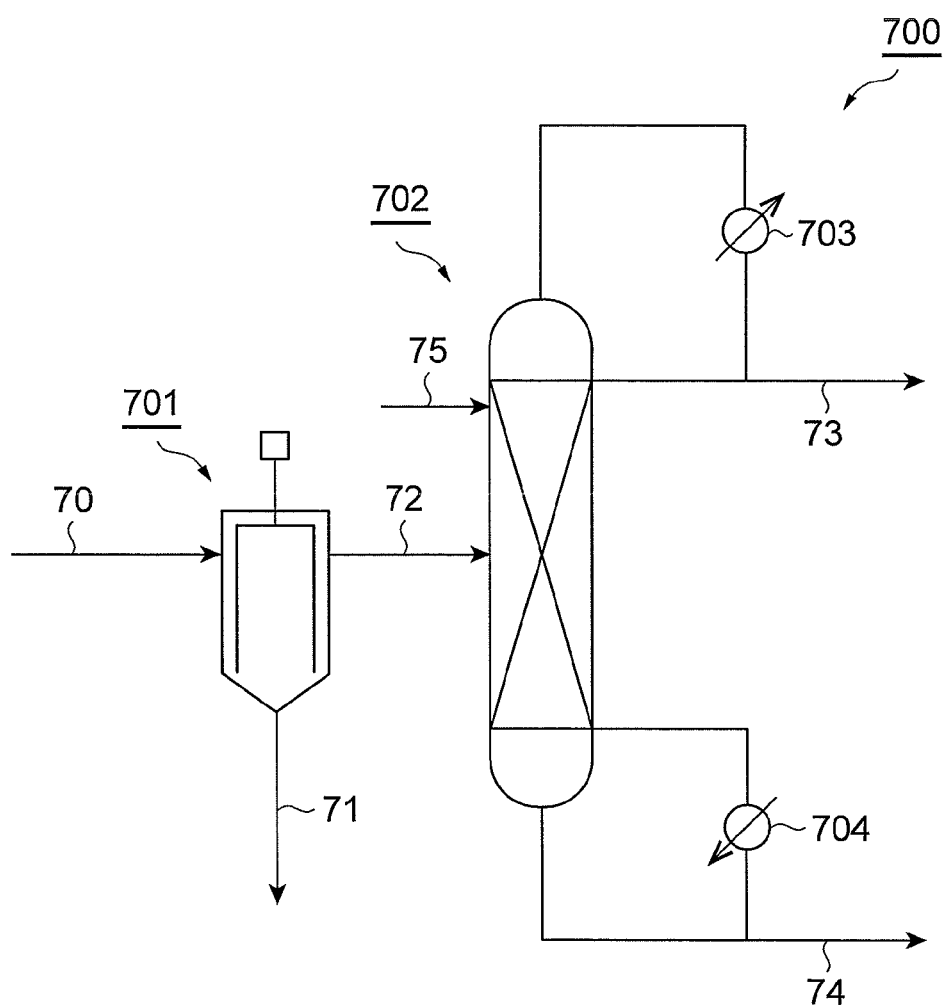
FIG. 7 is an illustration showing a distillation separation unit according to an embodiment.

Distillation separation was performed in a distillation separation unit 700 shown in FIG. 7.

The reaction solution obtained in Step (5-1) was heated to 150° C. and supplied to a thin film distillation apparatus 701 made of glass having an internal pressure of 0.1 kPa. The 4,4'-dicyclohexylmethanedi(carbamic acid butyl ester) was recovered from a line 71. The gas phase component containing the butylphenyl carbonate and the phenol was extracted from a line 72, supplied to a continuous multistage distillation column 702 packed with a Raschig ring made of Teflon®, and separated by distillation. The liquid obtained from a line 73 was the phenol, and the liquid obtained from a line 74 was the butylphenyl carbonate.

Reference Example 5

<Step (E-1)>

A mixture containing 4,4'-dicyclohexylmethanedi(carbamic acid butyl ester), butylphenyl carbonate and phenol was obtained by performing reaction similar to that in Step (5-1) of Example 5.

<Step (E-2)>

Figure 8:
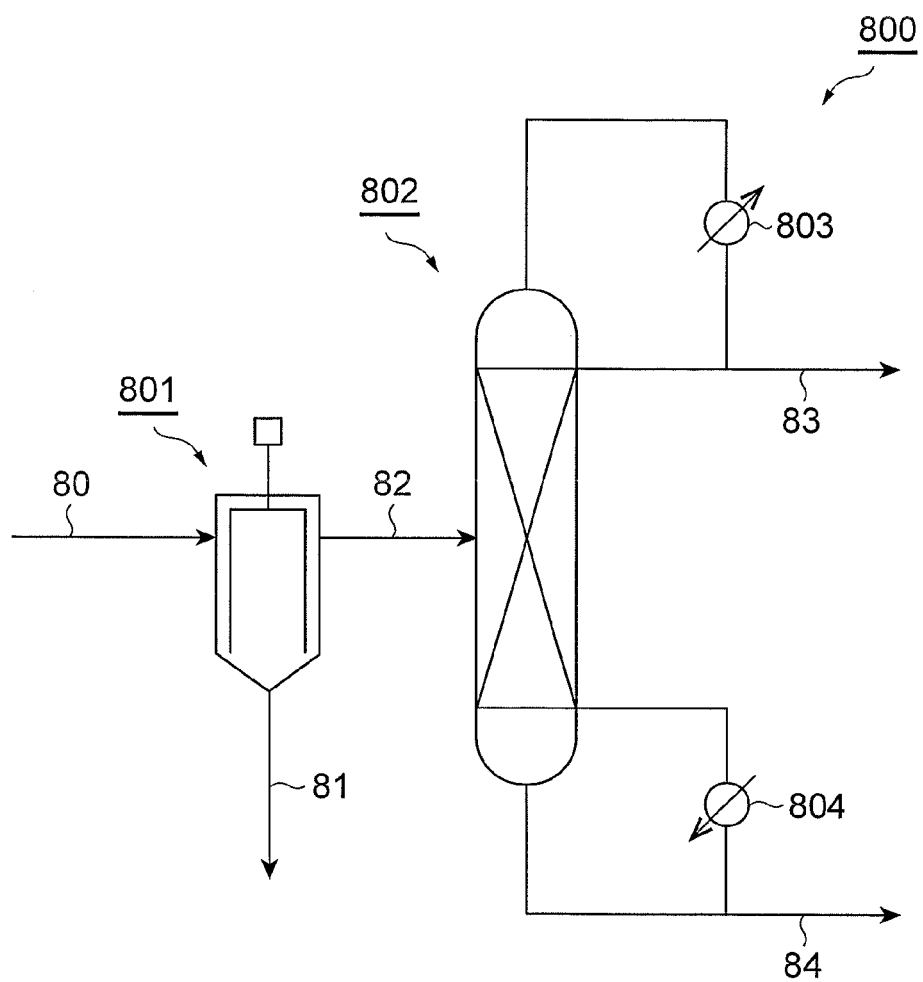
FIG. 8 is an illustration showing a distillation separation unit according to an embodiment.

Distillation separation was performed in a distillation separation unit 800 shown in FIG. 8.

The reaction solution obtained in Step (E-1) was heated to 150° C. and supplied to a thin film distillation apparatus 801 made of glass having an internal pressure of 0.1 kPa. The 4,4'-dicyclohexylmethanedi(carbamic acid butyl ester) was recovered from a line 81. The gas phase component containing the butylphenyl carbonate and the phenol was extracted from a line 82, supplied to a continuous multistage distillation column 802 packed with a Raschig ring made of titanium, and separated by distillation. The liquid obtained from a line 83 was a liquid containing the phenol and butanol, and the liquid obtained from a line 84 was a liquid containing the butylphenyl carbonate.

Presumably, in the continuous multistage distillation column 801, the titanium (Ti)-containing surface of the Raschig ring made of titanium promoted ester exchange reaction between butylphenyl carbonate and phenol, so that its product, diphenyl carbonate, was recovered from the bottom of the continuous multistage distillation column 801, and the other product, butanol, was recovered from the top of the continuous multistage distillation column 801.

Example 6

<Step (6-1)>

Figure 9:
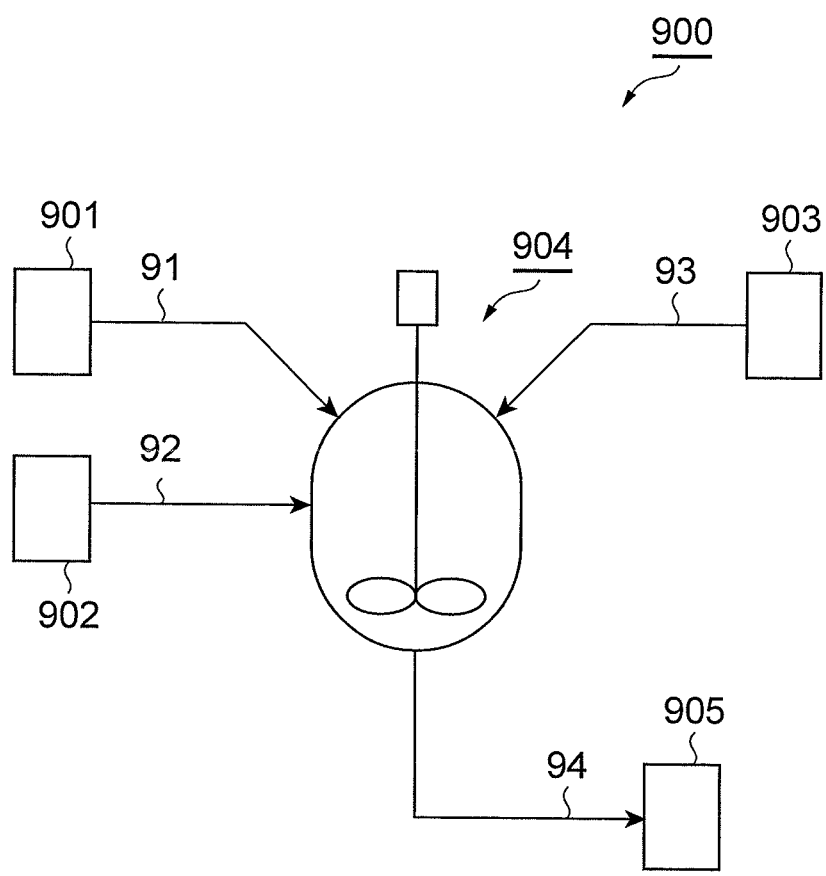
FIG. 9 is an illustration showing an N-substituted carbamic acid ester production unit according to an embodiment.

Step (6-1) was implemented using an N-substituted carbamic acid ester production unit 900 shown in FIG. 9.

With a line 94 closed, 25.7 kg (120 mol) of diphenyl carbonate was supplied from a storage tank 901 through a line 91 to a stirring tank 904, and 19.8 kg (110 mol) of phenol was from a storage tank 902 through a line 92 to the stirring tank 904. The liquid temperature in the stirring tank 904 was adjusted to about 50° C., and 4.9 kg (42 mol) of hexamethylenediamine was supplied from a storage tank 903 through a line 93 to the stirring tank 904. The results of analysis of the reaction solution by liquid chromatography showed that N,N'-hexanediyl-dicarbamic acid diphenyl ester was generated in a yield of 99.5%.

The line 94 was opened and the reaction solution was transferred through the line 94 to a storage tank 905. This operation was repeated five times.

<Step (6-2)>

Figure 10:
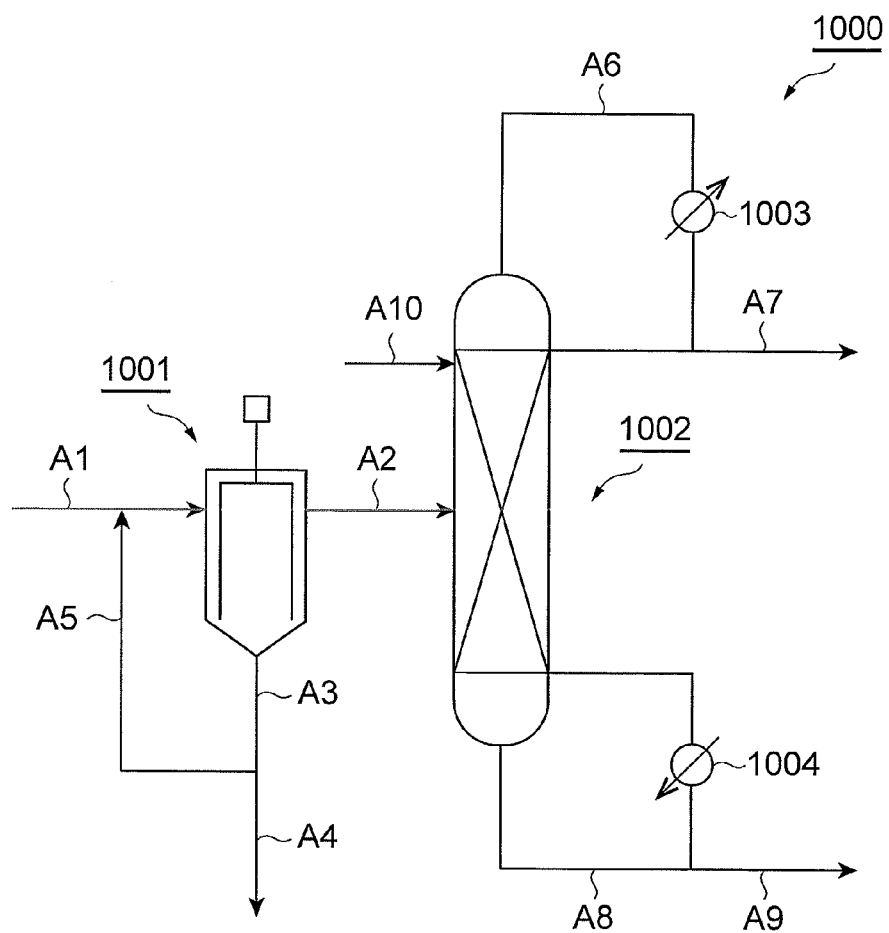
FIG. 10 is an illustration showing an N-substituted carbamic acid ester thermal decomposition and isocyanate separation unit according to an embodiment.

Step (6-2) was implemented using an N-substituted carbamic acid ester thermal decomposition and isocyanate separation unit 1000 shown in FIG. 10.

Hexamethylene diisocyanate was fed to the bottom of a continuous multistage packed column 1002 packed with a Raschig ring made of ceramic (Ti atom content: 0.809 mass %, Fe atom content: 0.699 mass %, Ni atom content: 0.01 mass %), and a total reflux operation for the hexamethylene diisocyanate was performed.

A thin film distillation apparatus 1001 made of glass was heated to 240° C., and its internal pressure was adjusted to about 1 kPa. The reaction solution recovered in the storage tank 905 in Step (6-1) was heated to 150° C. and supplied through a line A1 to the upper part of the thin film distillation apparatus 1001 at about 10 kg/hr. A mixture containing an isocyanate and a hydroxy compound was obtained by thermally decomposing the N,N'-hexanediyl-dicarbamic acid diphenyl ester in the thin film distillation apparatus 1001. The liquid phase component was extracted from a line A3 at the bottom of the thin film distillation apparatus 1001 and circulated through a line A5 and the line A1 to the upper part of the thin film distillation apparatus 1001. The mixture was extracted as the gas phase component from a line A2.

The mixture extracted as the gas phase component from the thin film distillation apparatus 1001 through the line A2 was continuously fed to the middle of the continuous multistage packed column 1002, and the mixture was separated by distillation. The gas distilled from the top of the continuous multistage packed column 1002 through a line A6 was condensed in a condenser 1003 and continuously extracted from a line A7. Meanwhile, the liquid phase component was extracted through lines A8 and A9.

The liquid extracted from the line A9 was a solution containing the hexamethylene diisocyanate at about 99 mass %. The yield based on hexamethylenediamine was 93%.

Example 7

<Step (7-1)>

Figure 11:
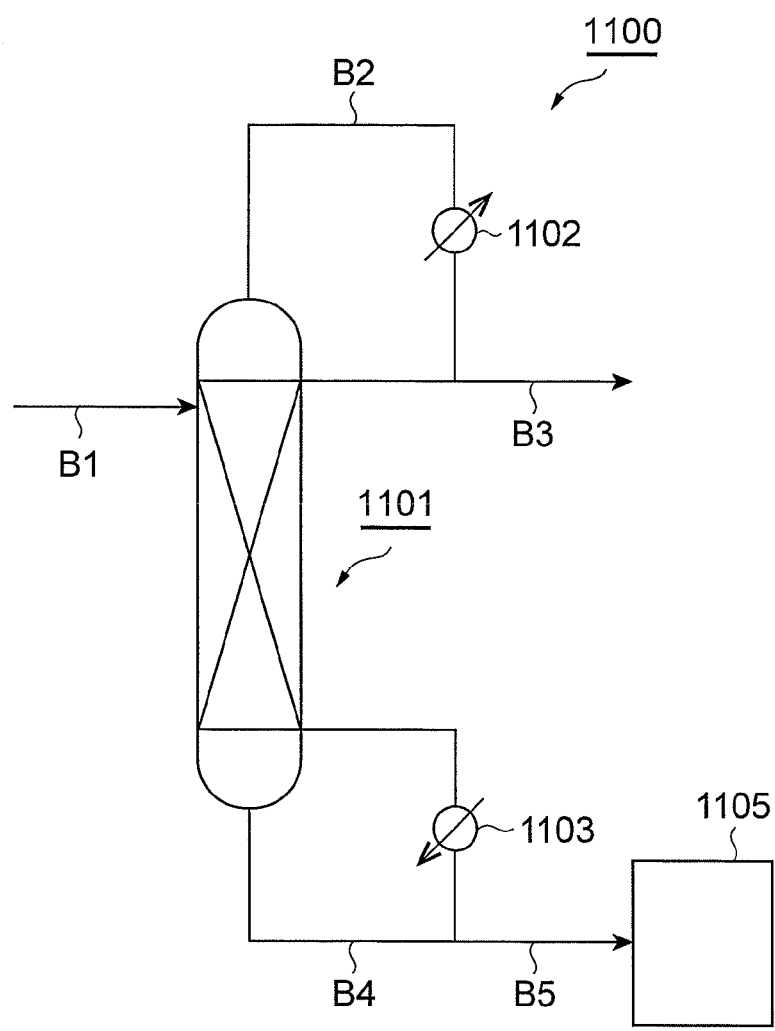
FIG. 11 is an illustration showing an N-substituted carbamic acid ester production unit according to an embodiment.

Step (7-1) was implemented using an N-substituted carbamic acid ester production unit 1100 shown in FIG. 11.

4.8 kg of hexamethylenediamine, 165 kg of 4-(1,1,3,3-tetramethylbutyl)phenol and 10.0 kg of urea were mixed to prepare a raw material solution. A packed column 1101 packed with a packing material (Heli Pack No. 3) was heated to 240° C., and its internal pressure was adjusted to about 20 kPa. A mixture having the same composition as that of the raw material solution was introduced into the packed column 1101 from a line B1 connected to the upper side of the packed column 1101. After the operation conditions were made stable, the raw material solution was introduced from the line B1 into the packed column 1101 and reacted. The reaction solution was recovered in a storage tank 1105 via lines B4 and B5 connected to the lowermost part of the packed column 1101. The gas phase component was recovered from a line B2 connected to the uppermost part of the packed column 1101 and condensed in a condenser 1102 maintained at about 85° C., and the resulting component was recovered. The reaction solution recovered from the line B5 was analyzed by liquid chromatography and $^1$H-NMR to find that N,N'-hexanediyl-dicarbamic acid di(4-(1,1,3,3-tetramethylbutyl)phenyl)ester was generated in the reaction solution in a yield of about 95% based on hexamethylenediamine.

This operation was repeated five times.

<Step (7-2)>

Figure 12:
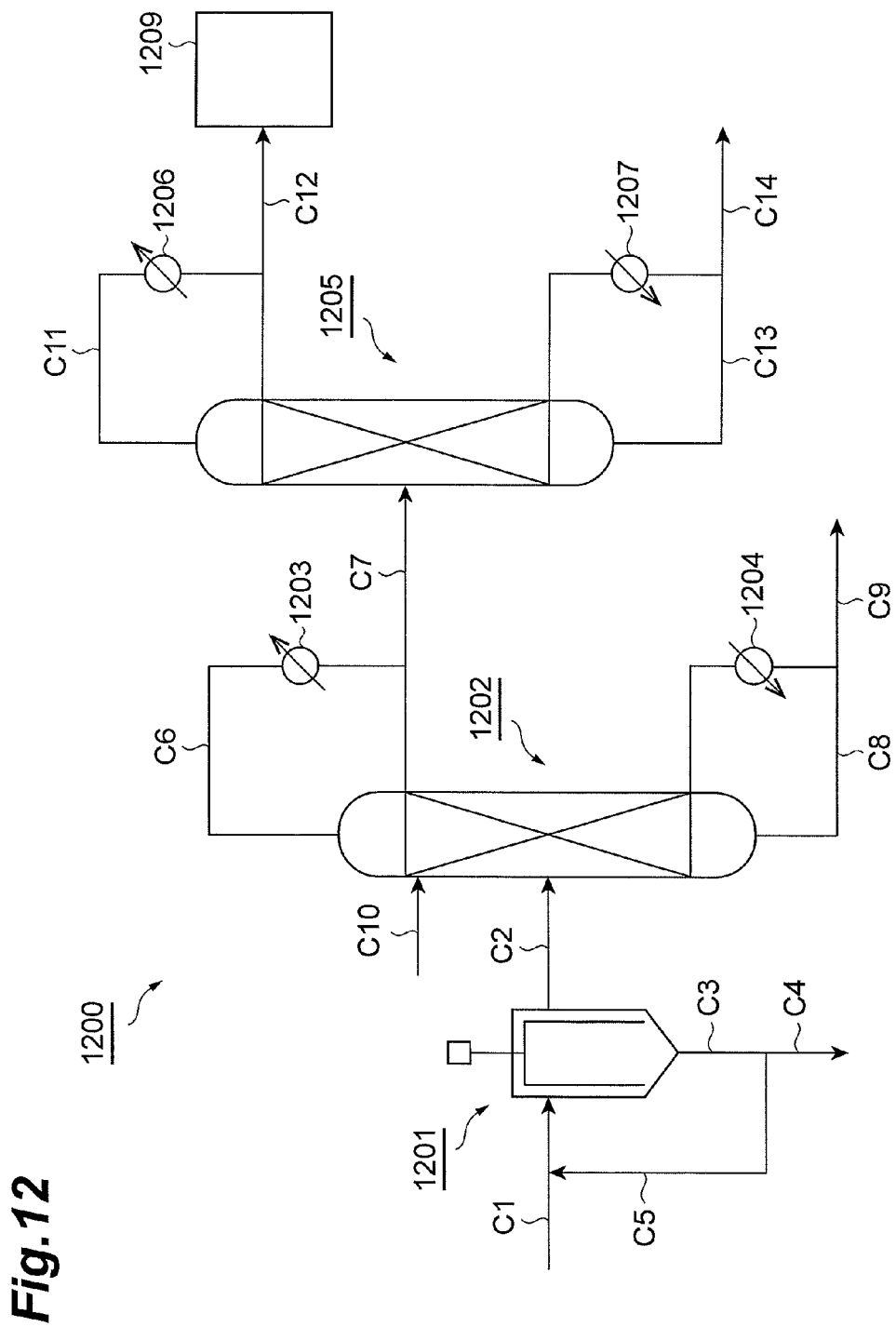
FIG. 12 is an illustration showing an N-substituted carbamic acid ester thermal decomposition and isocyanate separation unit according to an embodiment.

Step (7-2) was implemented using an N-substituted carbamic acid ester thermal decomposition and isocyanate separation unit 1200 shown in FIG. 12.

Hexamethylene diisocyanate was fed to the bottom of a continuous multistage packed column 1202 packed with a Raschig ring made of ceramic (Ti atom content: 0.809 mass %, Fe atom content: 0.699 mass %, Ni atom content: 0.01 mass %), and a total reflux operation for the hexamethylene diisocyanate was performed.

A thin film distillation apparatus 1201 was heated to 280° C., and its internal pressure was adjusted to about 1.0 kPa. The reaction solution recovered in the storage tank 1105 in Step (7-1) was heated to 150° C. and supplied to the thin film distillation apparatus 1201 at about 10 kg/hr from a line C1 connected to the upper side of the thin film distillation apparatus 1201, and the N,N'-hexanediyl-dicarbamic acid di(4-(1,1,3,3-tetramethylbutyl)phenyl)ester was thermally decomposed. A mixture containing an isocyanate and a hydroxy compound was obtained by this thermal decomposition. The liquid phase component was extracted from a line C3 connected to the bottom of the thin film distillation apparatus 1201, and introduced and circulated through a line C5 and the line C1 to the upper part of the thin film distillation apparatus 1201. The mixture was extracted as the gas phase component from a line C2.

The mixture extracted as the gas phase component from the thin film distillation apparatus 1201 through the line C2 was continuously fed to the middle of the continuous multistage packed column 1202, and the mixture was separated by distillation. The amount of heat necessary for distillation separation was supplied by circulating the liquid in the lower part of the column through a reboiler 1204 and a line C8. The pressure at the top of the column was about 5 kPa. The gas distilled from the top of the continuous multistage packed column 1202 through a line C6 was condensed in a condenser 1203 to provide the liquid phase component, which was continuously extracted from a line C7 and supplied to a continuous multistage packed column 1205.

The liquid phase component extracted from the line C7 was continuously fed to the middle of the continuous multistage packed column 1205, and the liquid phase component was separated by distillation. The gas distilled from the top of the continuous multistage packed column 1205 was condensed in a condenser 1206 and continuously extracted to a storage tank 1209. The liquid extracted to the storage tank 1209 was a solution containing the hexamethylene diisocyanate at about 99 mass %. The yield based on hexamethylenediamine was 88%.

Reference Example 6

<Step (F-1)>
N,N'-Hexanediyl-dicarbamic acid di(4-(1,1,3,3-tetramethylbutyl)phenyl)ester was obtained in a yield of about 95% based on hexamethylenediamine by performing reaction similar to that in Step (7-1) of Example 7.

<Step (F-2)>
An N-substituted carbamic acid ester thermal decomposition and isocyanate separation unit 1200 shown in FIG. 12 was used.

A method similar to that of Step (7-2) of Example 7 was performed, except that a continuous multistage packed column 1202 was packed with a Raschig ring made of SUS316 (Fe atom content: 67 mass % or more, Ni atom content: 12 mass %). The liquid recovered in a storage tank 1209 was a solution containing the hexamethylene diisocyanate at about 99.8 mass %. The yield based on hexamethylenediamine was 5%.

Example 8, Example 9, Reference Examples 7 to 10

Thermal decomposition of N,N'-Hexanediyl-dicarbamic acid di(4-(1,1,3,3-tetramethylbutyl)phenyl)ester and separation and recovery of isocyanate were performed in the same manner as in Step (7-2) of Example 7, except that the Raschig made of ceramic in Step (7-2) of Example 7 was changed to a packing material (Raschig ring) whose Fe atom content, Ni atom content and Ti atom content are as described in the following Table 1, respectively. The yield of the recovered hexamethylene diisocyanate based on hexamethylenediamine was as described in the following Table 1.

TABLE 1

|  | Example 8 | Example 9 | Reference Example 7 | Reference Example 8 | Reference Example 9 | Reference Example 10 |
|---|---|---|---|---|---|---|
| Fe atom content | 4.3 mass % | 8.5 mass % | 12.3 mass % | 7.8 mass % | 8.8 mass % | 13.1 mass % |
| Ni atom content | 3.8 mass % | 7.9 mass % | 8.3 mass % | 11.3 mass % | 9.0 mass % | 11.9 mass % |
| Ti atom content | 3.3 mass % | 9.1 mass % | 8.3 mass % | 8.9 mass % | 11.1 mass % | 12.1 mass % |
| Yield | 81% | 73% | 22% | 19% | 25% | 11% |

Example 10

<Step (10-1)>
68.0 kg of 4-(α,α-dimethylbenzyl)phenol and 7.0 kg of urea were supplied to a stirring tank, and the stirring tank was heated to 100° C. After the solution was made homogeneous, 3.3 kg of hexamethylenediamine was supplied at about 0.1 kg/min. After the supply of hexamethylenediamine was completed, stirring was performed for about two hours, and the reaction solution was analyzed by liquid chromatography, and the result showed that 1,6-hexanediurea was generated.

Figure 13:
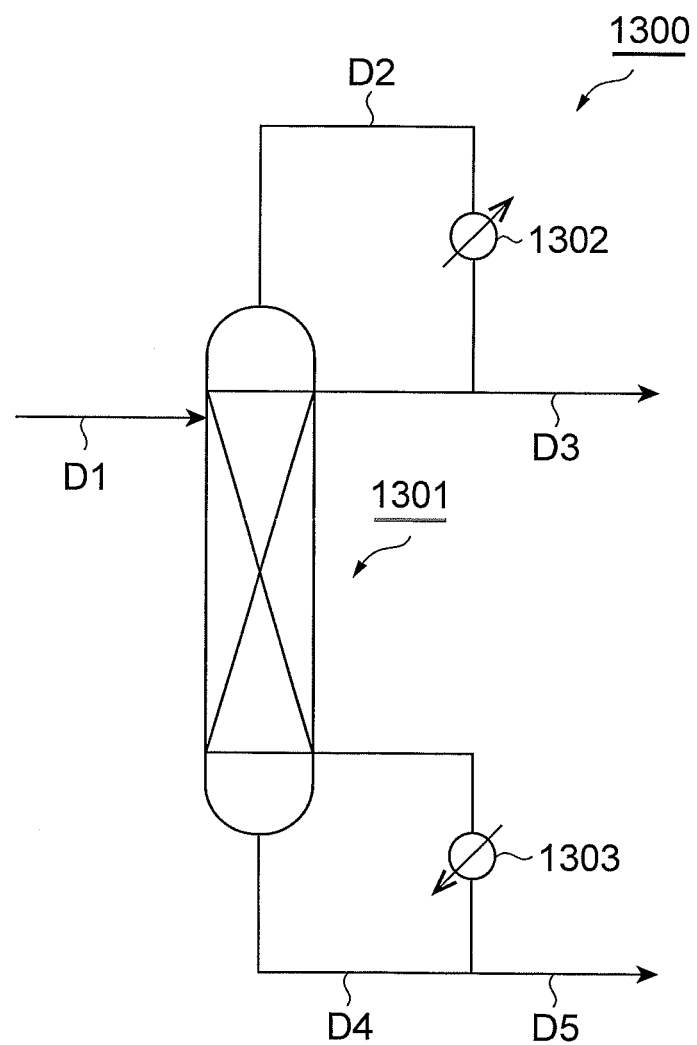
FIG. 13 is an illustration showing an N-substituted carbamic acid ester production unit according to an embodiment.

<Step (10-2)>
Step (10-2) was implemented using an N-substituted carbamic acid ester production unit 1300 shown in FIG. 13.

A packed column 1301 packed with a packing material (Heli Pack No. 3) was heated to 240° C., and the pressure within the packed column 1301 was adjusted to about 5 kPa. The reaction solution of Step (10-1) was introduced into the packed column 1301 from a line D1 connected to the upper side of the packed column 1301, and was reacted. The reaction solution was recovered via lines D4 and D5 connected to the lowermost part of the packed column 1101. The gas phase component was recovered from a line D2 connected to the uppermost part of the packed column 1301 and condensed in a condenser 1302 maintained at about 85° C., and the resulting component was recovered from a line D3. The reaction solution recovered from the line D5 was analyzed by liquid chromatography and $^1$H-NMR to find that N,N'-hexanediyl-dicarbamic acid di(4-(α,α-dimethylbenzyl)phenyl)ester was generated in the reaction solution in a yield of about 94% based on hexamethylenediamine.

Figure 14:
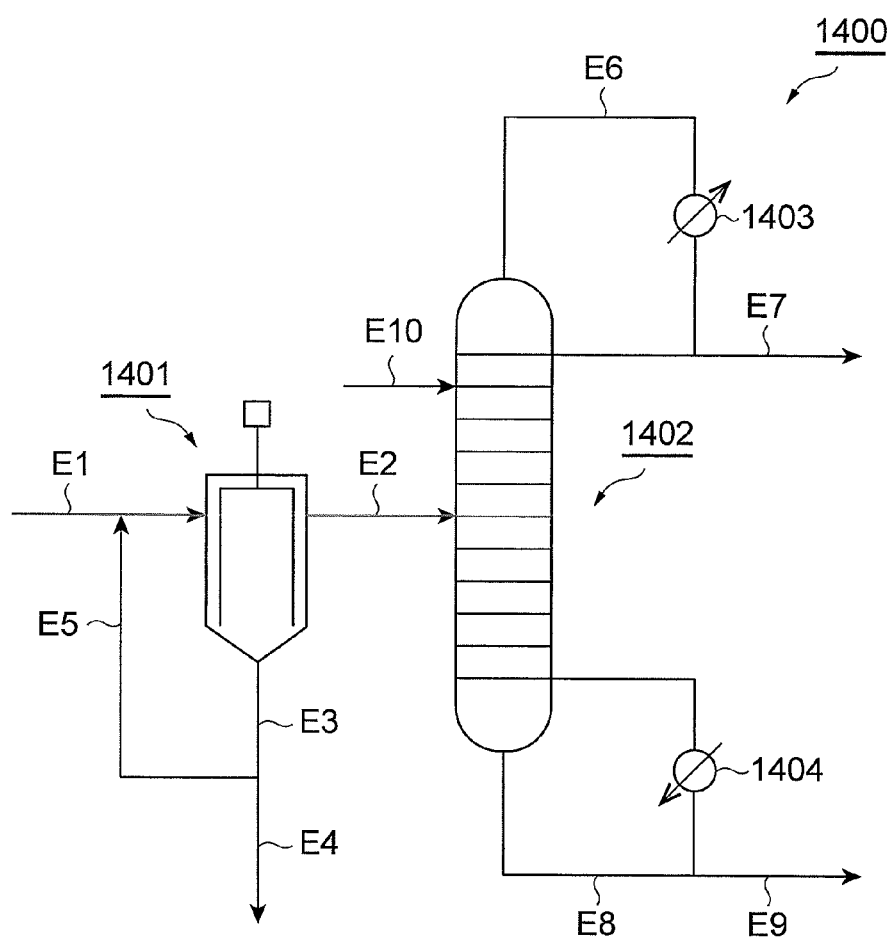
FIG. 14 is an illustration showing an N-substituted carbamic acid ester thermal decomposition and isocyanate separation unit according to an embodiment.

<Step (10-3)>
An N-substituted carbamic acid ester thermal decomposition and isocyanate separation unit 1400 shown in FIG. 14 was used.

The ratio of the (X) (unit: m$^2$) to the (Y) (unit: m$^3$) in a plate column 1402 (made of SUS316) was (X)/(Y)=41.

The reaction solution obtained in Step (10-2) was heated to 220° C. and supplied to a thin film distillation apparatus 1401 having an internal pressure of 0.1 kPa from a line E1 at about 30 g/min. The liquid phase component was extracted from the bottom of the thin film distillation apparatus 1401, and recirculated through a line E5 to the thin film distillation apparatus 1401, while a part of the liquid phase component was blown down from a line E4. Meanwhile, the gas phase component was extracted from a line E2 and separated by distillation in the plate column 1402. The gas extracted from the top of the plate column 1402 was condensed in a condenser 1403, and the condensate was refluxed to the plate column 1402 and also extracted from a line E7. The liquid extracted from the line E7 was a solution containing the hexamethylene diisocyanate at 99 mass %, and the yield based on hexamethylenediamine was 88%.

Examples 11 to 13, Reference Example 11, Reference Example 12

A method similar to that of Step (10-3) of Example 10 was performed except that the ratio of the (X) (unit: m$^2$) to the (Y) (unit: m$^3$) in a plate column 1402 (made of SUS316) was changed as shown in Table 2. The yield of the recovered hexamethylene diisocyanate based on hexamethylenediamine was as described in the following Table 2.

TABLE 2

|  | Example 11 | Example 12 | Example 13 | Reference Example 11 | Reference Example 12 |
|---|---|---|---|---|---|
| (X)/(Y) | 55 | 68 | 75 | 110 | 208 |
| Yield (%) | 73% | 67% | 55% | 28% | 24% |

Example 14

A method similar to that of Step (7-2) of Example 7 was performed, except that pentadecane was supplied from a line C10. The liquid phase component was sampled from a sampling line at a middle position between the part connected with a line C2 and the bottom in a continuous multistage packed column 1202, and was analyzed to find that it contained the pentadecane at 10 mass %. Meanwhile, the gas phase component extracted from a line C6 connected to the top of the continuous multistage packed column 1202 was condensed in a condenser 1203, and the condensate was refluxed to the continuous multistage packed column 1202, while a portion thereof was extracted from a line C7. The liquid extracted from the line C7 was analyzed to find that it was a mixture containing the pentadecane at 45 mass % and the hexamethylene diisocyanate at 54 mass %. The mixture was further separated by distillation to recover the hexamethylene diisocyanate, and the hexamethylene diisocyanate was obtained in a yield of 94% based on hexamethylenediamine.

When the normal boiling point of pentadecane (Tc), the normal boiling point of hexamethylene diisocyanate (Tb) and the normal boiling point of 4-(1,1,3,3-tetramethylbutyl) phenol (Ta) were compared, Tb<Tc<Ta was satisfied.

Example 15

A method similar to that of Step (10-3) of Example 10 was performed, except that benzyltoluene (isomer mixture) was supplied from a line E10. The liquid phase component was sampled from a sampling line at a middle position between the part connected with a line E2 and the bottom in a plate column 1402, and was analyzed to find that it contained the benzyltoluene at 24 mass %. Meanwhile, the gas phase component extracted from a line E6 connected to the top of the plate column 1402 was condensed in a condenser 1403, and the condensate was refluxed to the plate column 1402, while a portion thereof was extracted from a line E7. The liquid extracted from the line E7 was analyzed to find that it was a mixture containing the benzyltoluene at 53 mass % and the hexamethylene diisocyanate at 46 mass %. The mixture was further separated by distillation to recover the hexamethylene diisocyanate, and the hexamethylene diisocyanate was obtained in a yield of 93% based on hexamethylenediamine.

When the normal boiling point of benzyltoluene (Tc), the normal boiling point of hexamethylene diisocyanate (Tb) and the normal boiling point of 4-(α,α-dimethylbenzyl) phenol (Ta) were compared, Tb<Tc<Ta was satisfied.

Example 16

Step (16-1)

An N-substituted carbamic acid ester thermal decomposition and isocyanate separation unit 1400 shown in FIG. 14 was used.

n-Dodecane was supplied to the bottom of a plate column 1402, and a total reflux operation for n-dodecane was performed at a column top pressure of about 1 kPa.

A thin film distillation apparatus 1401 was heated to 290° C., and its internal pressure was adjusted to about 2 kPa. A mixture of N,N'-hexanediyl-bis-thiocarbamic acid di(O-(4-(1,1,3,3-tetramethylbutyl)phenyl)) and phenol (mass ratio 10:1) was supplied to the upper part of the thin film distillation apparatus 1401 through a line E1 at about 1.0 kg/hr, and the N,N'-hexanediyl-bis-thiocarbamic acid di(O-(4-(1,1,3,3-tetramethylbutyl)phenyl)) was thermally decomposed. The liquid phase component was extracted from a line E3 at the bottom of the thin film distillation apparatus 1401. The mixed gas was extracted from a line E2.

The mixed gas extracted from the thin film distillation apparatus 1401 through the line E2 was continuously fed to the middle of the plate column 1402, and at the same time, n-dodecane was supplied from a line E10. The liquid phase component was sampled from a sampling line at a middle position between the part connected with the line E2 and the bottom in the plate column 1402, and was analyzed to find that it contained the n-dodecane at 14 mass %.

The gas phase component distilled from the top of the plate column 1402 was condensed in a condenser 1403, and the condensate was continuously extracted from a line E7, while a portion thereof was refluxed to the plate column 1402. The liquid extracted from the line E7 was a mixture containing the n-dodecane and hexamethylene diisothiocyanate. Meanwhile, the liquid phase component was extracted through lines E8 and E9. The liquid extracted from the line E9 was 4-(1,1,3,3-tetramethylbutyl)phenol. The liquid extracted from the line E7 was analyzed and the result showed that the yield of the hexamethylene diisothiocyanate based on N,N'-hexanediyl-bis-thiocarbamic acid di(O-phenyl) was 89%.

When the normal boiling point of hexamethylene diisothiocyanate was defined as Tb and the normal boiling point of 4-(1,1,3,3-tetramethylbutyl)phenol was defined as Ta, the normal boiling point Tc of n-dodecane satisfied Tb<Tc<Ta.

Example 17

<Step (17-1)>

A method similar to that of Step (16-1) of Example 16 was performed, except that a mixture of N,N'-hexanediyl-bis-thiocarbamic acid di(S-phenyl) and benzenethiol (mass ratio 10:1) was used in place of a mixture of N,N'-hexanediyl-bis-thiocarbamic acid di(O-phenyl) and phenol.

The liquid phase component was sampled from a sampling line at a middle position between the part connected with a line E2 and the bottom in a plate column 1402, and was analyzed to find that it contained n-dodecane at 15 mass %.

The gas phase component distilled from the top of the plate column 1402 was condensed in a condenser 1403, and the condensate was continuously extracted from a line E7, while a portion thereof was refluxed to the plate column 1402. The liquid extracted from the line E7 was a mixture containing the n-dodecane and benzenethiol. Meanwhile, the liquid phase component was extracted through lines E8 and E9. The liquid extracted from the line E9 was hexamethylene diisocyanate. The yield of the hexamethylene diisocyanate based on N,N'-hexanediyl-bis-thiocarbamic acid di(S-phenyl) was 91%.

When the normal boiling point of hexamethylene diisocyanate was defined as Tb and the normal boiling point of benzenethiol was defined as Ta, the normal boiling point Tc of n-dodecane satisfied Ta<Tc<Tb.

Example 18

<Step (18-1)>

A method similar to that of Step (16-1) of Example 16 was performed, except that n-decane was used in place of n-dodecane, and a mixture of N,N'-hexanediyl-bis-dithiocarbamic acid diphenyl and benzenethiol (mass ratio 8:1) was used in place of a mixture of N,N'-hexanediyl-bis-thiocarbamic acid di(O-phenyl) and phenol.

The liquid phase component was sampled from a sampling line at a middle position between the part connected with a line E2 and the bottom in a plate column 1402, and was analyzed to find that it contained n-decane at 18 mass %.

The gas phase component distilled from the top of the plate column 1402 was condensed in a condenser 1403, and the condensate was continuously extracted from a line E7, while a portion thereof was refluxed to the plate column 1402. The liquid extracted from the line E7 was a mixture containing the n-decane and benzenethiol. Meanwhile, the liquid phase component was extracted through lines E8 and E9. The liquid extracted from the line E9 was hexamethylene diisothiocyanate. The yield of the hexamethylene diisothiocyanate based on N,N'-hexanediyl-bis-dithiocarbamic acid diphenyl was 87%.

When the normal boiling point of hexamethylene diisothiocyanate was defined as Tb and the normal boiling point of benzenethiol was defined as Ta, the normal boiling point Tc of n-decane satisfied Ta<Tc<Tb.

INDUSTRIAL APPLICABILITY

The separation method of the present invention enables efficient separation of a mixture containing a plurality of compounds that reversibly react with each other. Therefore, the separation method of the present invention is highly industrially useful and commercially valuable.

REFERENCE SIGNS LIST

100: Distillation separation unit
101: Continuous multistage packed column
102, 104: Condenser
103: Reboiler
10, 11, 12, 13, 14, 15, 16, 17, 18: Line
200: Distillation separation unit
201: Continuous multistage packed column
202, 204: Condenser
203: Reboiler
20, 21, 22, 23, 24, 25, 26, 27, 28: Line
300: Distillation separation unit
301: Thin film distillation apparatus
302: Continuous multistage distillation column
303: Condenser
304: Reboiler
30, 31, 32, 33, 34, 35, 36: Line
400: Distillation separation unit
401: Thin film distillation apparatus
402: Continuous multistage distillation column
403: Condenser
404: Reboiler
40, 41, 42, 43, 44, 45, 46: Line
500: Distillation separation unit
501: Continuous multistage packed column
502: Condenser
503: Reboiler
51, 52, 53, 54, 55: Line
600: Distillation separation unit
601: Continuous multistage packed column
602: Condenser
603: Reboiler
61, 62, 63, 64, 65: Line
700: Distillation separation unit
701: Thin film distillation apparatus
702: Continuous multistage distillation column
703: Condenser
704: Reboiler
70, 71, 72, 73, 74, 75: Line
800: Distillation separation unit
801: Thin film distillation apparatus
802: Continuous multistage distillation column
803: Condenser
804: Reboiler
80, 81, 82, 83, 84: Line
900: N-substituted carbamic acid ester production unit
901, 902, 903, 905: Storage tank
904: Stirring tank
90, 91, 92, 93, 94: Line
1000: N-substituted carbamic acid ester thermal decomposition and isocyanate separation unit
1001: Thin film distillation apparatus
1002: Continuous multistage packed column
1003: Condenser
1004: Reboiler
A1, A2, A3, A4, A5, A6, A7, A8, A9, A10: Line
1100: N-substituted carbamic acid ester production unit
1101: Packed column
1102: Condenser
1103: Reboiler
1105: Storage tank
B1, B2, B3, B4, B5: Line
1200: N-substituted carbamic acid ester thermal decomposition and isocyanate separation unit
1201: Thin film distillation apparatus
1202, 1205: Continuous multistage packed column
1203, 1206: Condenser
1204, 1207: Reboiler
1209: Storage tank
C1, C2, C3, C4, C5, C6, C7, C8, C9, C10, C11, C12, C13, C14: Line
1300: N-substituted carbamic acid ester production unit
1301: Packed column
1302: Condenser
1303: Reboiler
D1, D2, D3, D4, D5: Line
1400: N-substituted carbamic acid ester thermal decomposition and isocyanate separation unit
1401: Thin film distillation apparatus
1402: Plate column
1403: Condenser
1404: Reboiler
E1, E2, E3, E4, E5, E6, E7, E8, E9, E10: Line

The invention claimed is:

1. A method of separating an active hydrogen-containing compound (A) and a compound (B) that reversibly reacts with (A), comprising:
a step of separating at least either (A) or (B) from a mixture containing (A) and (B) by distillation in a multistage distillation column; and
a step of supplying the mixture to an inactive region formed within the multistage distillation column, wherein:
the multistage distillation column is a plate column or a packed column; and
the inactive region is one plate in the plate column which a surface contacting with the mixture comprises a material inactive to a reaction between (A) and (B), or the inactive region is one theoretical plate in a packed column packed with a packing material comprising a material inactive to a reaction between (A) and (B),
wherein:
(i) the material inactive to a reaction between (A) and (B) is a material in which an Fe atom content, a Ni atom content and a Ti atom content are each 10 mass % or less; or
(ii) an area (X) (unit:m$^2$) of an inner surface of the inactive region contacting with the mixture and a volume (Y) (unit:m$^3$) of the mixture retained in the inactive region satisfy $(X)/(Y) \leq 100$, and
wherein:
the compound (A) contains a hydrogen atom bonded to a heteroatom or a halogen atom, and the compound (B) contains at least one group selected from the group consisting of formula (5), formula (6), formula(7) and formula (8):

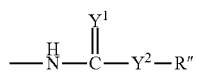 (5)

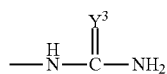 (6)

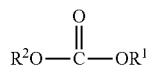 (7)

—N=C=Y$^4$ (8)

wherein:
Y$^1$, Y$^2$, Y$^3$ and Y$^4$ each represents an oxygen atom,
R$^1$ and R$^2$ each independently represents an organic group having 1 to 30 carbon atoms, and
R″ represents an organic group.

2. The method according to claim 1, wherein compound (A) contains at least one group selected from the group consisting of formula (1), formula (2), formula (3) and formula (4):

—NH$_2$ (1)

—X$^1$H (2)

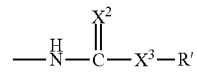 (3)

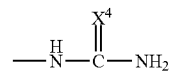 (4)

wherein:
X$^1$, X$^2$, X$^3$ and X$^4$ each independently represent an oxygen atom or a sulfur atom, and R′ represents an organic group.

3. The method according to claim 1, wherein the step of distillation separation is performed in the presence of a compound (C) that has a normal boiling point between a normal boiling point of (A) and a normal boiling point of (B) and is chemically inactive to (A) and (B).

4. The method according to claim 1, wherein the compound (A) is represented by the following formula (9):

$$R^4 +\!\!\!\!-(X^5-H)_a \quad (9)$$

wherein:
R$^3$ represents an organic group having 1 to 44 carbon atoms,
X$^5$ represents an oxygen atom or a sulfur atom, and
a represents an integer of 1 to 6.

5. The method according to claim 1, wherein the formula (8) of compound (B) has the following formula (10):

$$R^4 +\!\!\!\!-(N=C=Y^5)_b \quad (10)$$

wherein:
R$^4$ represents an organic group having 1 to 80 carbon atoms,
Y$^5$ represents an oxygen atom, and
b represents an integer of 1 to 10.

* * * * *